US009474836B2

(12) United States Patent
Locke et al.

(10) Patent No.: US 9,474,836 B2
(45) Date of Patent: Oct. 25, 2016

(54) REDUCED-PRESSURE CANISTERS AND METHODS FOR RECYCLING

(71) Applicant: KCI Licensing, Inc., San Antonio, TX (US)

(72) Inventors: Christopher Brian Locke, Bournemouth (GB); Jonathan Paul Jaeb, Boerne, TX (US); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 333 days.

(21) Appl. No.: 14/150,542

(22) Filed: Jan. 8, 2014

(65) Prior Publication Data
US 2014/0121617 A1 May 1, 2014

Related U.S. Application Data

(62) Division of application No. 13/108,719, filed on May 16, 2011, now Pat. No. 8,641,693.

(60) Provisional application No. 61/414,738, filed on Nov. 17, 2010, provisional application No. 61/345,821, filed on May 18, 2010, provisional application No. 61/345,830, filed on May 18, 2010.

(51) Int. Cl.
*A61M 27/00* (2006.01)
*B65D 79/02* (2006.01)
*A61M 1/00* (2006.01)

(52) U.S. Cl.
CPC ......... *A61M 1/0005* (2013.01); *A61M 1/0001* (2013.01); *A61M 1/0027* (2014.02);
(Continued)

(58) Field of Classification Search
USPC ........................................................ 206/592
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Lynne Anderson
*Assistant Examiner* — Paula L Craig

(57) ABSTRACT

Reduced-pressure canisters and methods for recycling are disclosed. In one instance, a method for performing multiple reduced pressure treatments on one or more patients includes providing a reduced-pressure treatment system that includes a first canister body, a fluid reservoir, and one or more modules, such as a pump control module. The method involves using the reduced-pressure system and then removing one or more modules and placing the one or more modules in fitted shipping receptacle that disallows shipping of the fluid reservoir. The one or more modules may be reconditioned and coupled to a second canister body. Other systems and methods are disclosed.

4 Claims, 13 Drawing Sheets

(52) U.S. Cl.
CPC .......... *A61M1/0072* (2014.02); *A61M 1/0031* (2013.01); *A61M 1/0088* (2013.01); *A61M 2205/273* (2013.01); *A61M 2205/3306* (2013.01); *A61M 2205/3317* (2013.01); *A61M 2205/3331* (2013.01); *A61M 2205/3344* (2013.01); *A61M 2205/8206* (2013.01); *A61M 2205/84* (2013.01); *A61M 2209/06* (2013.01); *Y10T 137/0402* (2015.04)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,690,315 A * | 9/1972 | Chittenden | A61F 5/441 206/363 |
| 3,826,254 A | 7/1974 | Mellor | |
| 3,948,436 A * | 4/1976 | Bambara | B65D 31/02 206/245 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,602,715 A * | 7/1986 | Sarver | B65D 81/05 206/515 |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,867,372 A * | 9/1989 | Patterson | B65D 5/4233 206/459.5 |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,117,976 A * | 6/1992 | Whitt | B65D 71/10 206/446 |
| 5,134,994 A | 8/1992 | Say | |
| 5,146,732 A * | 9/1992 | Grey | B65D 5/4233 53/171 |
| 5,149,331 A | 9/1992 | Ferdman et al. | |
| 5,156,277 A * | 10/1992 | Witz | B29C 51/26 206/524.1 |
| 5,167,613 A | 12/1992 | Karami et al. | |
| 5,176,663 A | 1/1993 | Svedman et al. | |
| 5,178,282 A * | 1/1993 | Williams | A61B 19/026 206/363 |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,736,098 A * | 4/1998 | Kerwin | B08B 9/08 134/26 |
| 5,742,883 A * | 4/1998 | Girard | G03G 21/181 229/301 |
| 5,829,229 A * | 11/1998 | Hyatt | B65D 1/36 53/445 |
| 5,839,058 A * | 11/1998 | Phillips | H04M 1/0202 455/409 |
| 5,860,555 A * | 1/1999 | Mayled | A61B 19/0287 220/495.05 |
| 5,965,858 A * | 10/1999 | Suzuki | G06K 17/00 209/630 |
| 6,071,267 A | 6/2000 | Zamierowski | |
| 6,109,444 A * | 8/2000 | Bagwell | B65D 81/025 206/588 |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,069,236 B1 * | 6/2006 | Tsunenari | G06Q 10/087 705/26.1 |
| 8,409,160 B2 * | 4/2013 | Locke | A61M 1/0066 137/205 |
| 8,641,693 B2 * | 2/2014 | Locke | A61M 1/0001 206/438 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0026620 A1 * | 2/2003 | Gallivan | B41J 2/17546 399/24 |
| 2003/0080023 A1 * | 5/2003 | Slot | B65D 81/133 206/588 |

(56) References Cited

U.S. PATENT DOCUMENTS

| | | | | |
|---|---|---|---|---|
| 2004/0000581 | A1* | 1/2004 | Brandolini | B31B 37/00 229/68.1 |
| 2005/0252792 | A1* | 11/2005 | Stennes | B65D 77/003 206/96 |
| 2005/0263589 | A1* | 12/2005 | Kikuchi | G06Q 10/08 235/383 |
| 2006/0079852 | A1 | 4/2006 | Bubb et al. | |
| 2008/0071216 | A1* | 3/2008 | Locke | A61M 5/1415 604/119 |
| 2008/0228103 | A1* | 9/2008 | Ritchie | A61B 10/0275 600/563 |
| 2008/0281301 | A1* | 11/2008 | DeBoer | G06F 19/3487 606/1 |
| 2009/0007525 | A1* | 1/2009 | Lewis | G06Q 30/02 53/474 |
| 2009/0035609 | A1* | 2/2009 | Ludtke | H01M 10/48 429/10 |
| 2009/0036873 | A1* | 2/2009 | Nielsen | A61M 1/0031 604/543 |
| 2010/0001055 | A1* | 1/2010 | Watterson | B65D 5/10 229/117.27 |
| 2011/0049004 | A1* | 3/2011 | Mena | B65D 5/48024 206/592 |
| 2013/0190707 | A1* | 7/2013 | Locke | A61M 1/0066 604/319 |

FOREIGN PATENT DOCUMENTS

| | | | |
|---|---|---|---|
| AU | 755496 | 2/2002 | |
| CA | 2005436 | 6/1990 | |
| DE | 26 40 413 A1 | 3/1978 | |
| DE | 43 06 478 A1 | 9/1994 | |
| DE | 295 04 378 U1 | 10/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 B1 | 8/2004 | |
| EP | 2100562 A2 * | 9/2009 | A61B 17/07207 |
| GB | 692578 | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 B | 3/1999 | |
| GB | 2 333 965 A | 8/1999 | |
| JP | 4129536 | 4/1992 | |
| SG | 71559 | 4/2002 | |
| WO | 80/02182 | 10/1980 | |
| WO | 87/04626 | 8/1987 | |
| WO | 90/10424 | 9/1990 | |
| WO | 93/09727 | 5/1993 | |
| WO | 94/20041 | 9/1994 | |
| WO | 96/05873 | 2/1996 | |
| WO | 97/18007 | 5/1997 | |
| WO | 99/13793 | 3/1999 | |

OTHER PUBLICATIONS

Louis C. Argenta, MD and Michael J. Morykwas, PhD; "Vacuum-Assisted Closure: a New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Dukić, Ž. Maksimović, D. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin

(56) References Cited

OTHER PUBLICATIONS (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

REDUCED-PRESSURE CANISTERS AND METHODS FOR RECYCLING

RELATED APPLICATIONS

This Application is a divisional of U.S. patent application Ser. No. 13/108,719 entitled "Reduced-Pressure Canisters and Methods for Recycling," filed 16 May 2011 which claims the benefit, under 35 USC §119(e), of the filing of U.S. Provisional Patent Application Ser. No. 61/414,738, entitled "Reduced-Pressure Canisters and Methods for Recycling," filed 17 Nov. 2010, which is incorporated herein by reference for all purposes; U.S. Provisional Patent Application Ser. No. 61/345,830, entitled "Systems and Methods for Measuring Reduced Pressure Employing An Isolated Fluid Path," filed 18 May 2010, which is incorporated herein by reference for all purposes; and U.S. Provisional Patent Application Ser. No. 61/345,821, entitled "Reduced-Pressure Treatment Systems and Methods Employing A Fluidly Isolated Pump Control Unit," filed 18 May 2010, which is incorporated herein by reference for all purposes.

BACKGROUND

The present disclosure relates generally to reduced-pressure medical treatment systems and, more particularly, but not by way of limitation, to reduced-pressure canisters, methods, and systems.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue.

SUMMARY

According to an illustrative, non-limiting embodiment, a reduced-pressure treatment device for use with a system for treating a tissue site on a patient with reduced pressure includes a canister unit having a pump head with at least one diaphragm, wherein the pump head is fluidly coupled to the tissue site to provide reduced pressure to the tissue site, and a fluid reservoir fluidly coupled to the pump head for collecting fluid from the tissue site. The reduced-pressure treatment device also includes a pump control unit fluidly separate from the canister unit and operable to provide pump energy to the pump head to cause the pump head to generate reduced pressure. The pump control unit may have a control device and a power system for providing power to the control device. The reduced-pressure treatment device further includes at least one linking interface associated with the canister unit and the pump control unit. The linking interface provides the pump energy to the pump head to generate reduced pressure.

According to another illustrative, non-limiting embodiment, a reduced-pressure treatment system for providing reduced-pressure treatment to a tissue site on a patient includes a manifold for disposing proximate the tissue site, a sealing member for placing over the tissue site and the manifold and operable to form a fluid seal, and a reduced-pressure treatment device. The reduced-pressure treatment device includes a canister unit having a pump head with at least one diaphragm, wherein the pump head is for fluidly coupling to the tissue site to provide reduced pressure to the tissue site, and a fluid reservoir fluidly coupled to the pump head for collecting fluid from the tissue site. The reduced-pressure treatment device also includes a pump control unit that is fluidly separate from the canister unit and operable to provide the pump energy to the pump head to cause the pump head to generate reduced pressure. The pump control unit may have a control device and a power system for providing power to the control device. The reduced-pressure treatment device further includes at least one linking interface associated with the canister unit and the pump control unit. The linking interface provides energy to the pump head to generate reduced pressure.

According to another illustrative, non-limiting embodiment a method of providing reduced-pressure treatment to a tissue site on a patient includes the steps of placing a manifold proximate the tissue site, disposing a sealing member over the manifold and a patient's epidermis, forming a fluid seal between the sealing member and the patient's epidermis, and delivering reduced pressure to the manifold. The step of delivering reduced pressure to the manifold includes providing an electrical current to a first electromagnet that is substantially aligned with a diaphragm. The first electromagnet is fluidly isolated from the diaphragm. The first electromagnet deflects the diaphragm from a first position to a second position, and the movement of the diaphragm between the first position and the second position causes fluid movement to generate reduced pressure.

According to another illustrative, non-limiting embodiment, a method for performing multiple reduced pressure treatments on one or more patients includes providing a reduced-pressure treatment system. The reduced-pressure treatment system includes a first canister body formed with a fluid reservoir, a conduit fluidly coupled to the fluid reservoir for delivering fluids to the fluid reservoir from the patient, a pump attached to the first canister body and operable to develop a reduced pressure within the fluid reservoir, a removable power-and-control unit coupled to the pump for activating and controlling the pump, and a fitted shipping receptacle for receiving and holding the power-and-control unit during shipment to a recycling center. The removable power-and-control unit is operable to be removed by a user. The method further includes using the reduced-pressure treatment system to remove fluids from the patient, removing the power-and-control unit from the first canister after use, and placing power-and-control unit in the fitted shipping receptacle and shipping to a reconditioning center. The method may also include reconditioning the power-and-control unit and removeably coupling the power-and-control unit to a second canister housing.

According to another illustrative, non-limiting embodiment, a fluid collection system for use with patients undergoing reduced pressure treatment includes a canister body formed with a fluid reservoir, a conduit fluidly coupled to the fluid reservoir for delivering fluids to the fluid reservoir from the patient, a pump attached to the canister body and operable to develop a reduced pressure within the fluid reservoir, and a removable power-and-control unit coupled to the pump for activating and controlling the pump. The removable power-and-control unit is operable to be removed by user. The fluid collection system may further include a fitted shipping receptacle for receiving and holding the power-and-control unit during shipment to a recycling center.

According to another illustrative, non-limiting embodiment, a method for performing multiple reduced pressure treatments on one or more patients includes providing a reduced-pressure treatment system. The reduced-pressure treatment system includes a first canister body formed with a fluid reservoir, a conduit fluidly coupled to the fluid reservoir for delivering fluids to the fluid reservoir from the patient, a pump attached to the first canister body and operable to develop a reduced pressure within the fluid reservoir, a control unit coupled to the pump for controlling the pump, and a removable power unit coupled to the pump for activating the pump. The removable power unit is operable to be removed by a user. The reduced-pressure treatment system also may include a fitted shipping receptacle for receiving and holding the power unit during shipment to a recycling center. The method further includes using the reduced-pressure system to remove fluids from the patient, removing the power unit from the first canister after use, placing power unit in the fitted shipping receptacle and shipping to a reconditioning center. The method may also include reconditioning the power unit, and removeably coupling the power unit to a second canister housing.

According to another illustrative, non-limiting embodiment, a fluid collection system for use with patients undergoing reduced pressure treatment includes a first canister body formed with a fluid reservoir, a conduit fluidly coupled to the fluid reservoir for delivering fluids to the fluid reservoir from the patient, a pump attached to the first canister body and operable to develop a reduced pressure within the fluid reservoir, a control unit coupled to the pump for controlling the pump, and a removable power unit coupled to the pump for activating the pump. The removable power unit is operable to be removed by a user. The system further includes a fitted shipping receptacle for receiving and holding the power unit during shipment to a recycling center.

According to another illustrative, non-limiting embodiment, a method for performing multiple reduced pressure treatments on one or more patients includes providing a reduced-pressure treatment system. The reduced-pressure system includes a first canister body formed with a fluid reservoir, a conduit fluidly coupled to the fluid reservoir for delivering fluids to the fluid reservoir from the patient, and a removable pump coupled to the first canister body and operable to develop a reduced pressure within the fluid reservoir. The removable pump is operable to be removed by a user. The reduced-pressure system further includes a removable power-and-control unit coupled to the pump for activating and controlling the pump. The removable power-and-control unit is operable to be removed by a user. The reduced-pressure system further includes a fitted shipping receptacle for receiving and holding the pump and power-and-control unit during shipment to a recycling center. The method further includes using the reduced-pressure system to remove fluids from the patient, removing the pump and the power-and-control unit from the first canister after use and placing the pump and the power-and-control unit in the fitted shipping receptacle and shipping to a reconditioning center. The method may further include reconditioning the pump and power-and-control unit and removeably coupling the pump and power-and-control unit to a second canister housing.

According to another illustrative, non-limiting embodiment, a fluid collection system for use with patients undergoing reduced pressure treatment includes a first canister body formed with a fluid reservoir, a conduit fluidly coupled to the fluid reservoir for delivering fluids to the fluid reservoir from the patient, and a removable pump coupled to the first canister body and operable to develop a reduced pressure within the fluid reservoir. The removable pump is operable to be removed by a user. The fluid collection system further includes a removable power-and-control unit coupled to the pump for activating and controlling the pump. The removable power-and-control unit is operable to be removed by a user. The fluid collection system further includes a fitted shipping receptacle for receiving and holding the pump and power-and-control unit during shipment to a recycling center.

According to another illustrative, non-limiting embodiment, a fluid collection system for use with patients undergoing reduced pressure treatment includes a canister unit formed with a fluid reservoir, a conduit fluidly coupled to the fluid reservoir for delivering fluids to the fluid reservoir from the patient, a connection member, and a pump control unit coupled by the connection member to the canister unit. The pump control unit includes a pump, control electronics for controlling the pump, and a power unit. The pump is fluidly coupled to the fluid reservoir and is operable to develop a reduced pressure within the fluid reservoir. The connection is operable to selectively hold the pump control unit and the canister unit in relative positions and to selectively allow separation of the pump control unit and the canister unit.

According to another illustrative, non-limiting embodiment, a method for performing multiple reduced pressure treatments on one or more patients includes providing a reduced-pressure treatment system. The reduced-pressure treatment system includes a canister unit formed with a fluid reservoir, a conduit fluidly coupled to the fluid reservoir for delivering fluids to the fluid reservoir from the patient, a connection member, and a pump control unit coupled by the connection member to the canister unit. The pump control unit includes a pump, control electronics for controlling the pump, and a power unit. The pump is fluidly coupled to the fluid reservoir and is operable to develop a reduced pressure within the fluid reservoir. The connection member is operable to selectively hold the pump control unit and the canister unit in relative positions and to selectively allow separation of the pump control unit and the canister unit. The method further includes using the reduced-pressure treatment system to collect fluids, disconnecting the connection member such that pump control unit is separate from the canister unit, disposing of the canister unit, and shipping the pump control unit to a recycling center for use with a second canister unit.

Other features and advantages of the illustrative embodiments will become apparent with reference to the drawings and the detailed description that follow.

BRIEF DESCRIPTION OF THE DRAWINGS

FIG. 14A is a schematic diagram of an illustrative, non-limiting embodiment of a first portion of another illustrative fitted shipping receptacle;

FIG. 14B is a schematic perspective view of an illustrative, non-limiting embodiment of a second portion of a fitted shipping receptacle, wherein the second portion is sized and configured to mate the first portion shown in FIG. 14A;

DETAILED DESCRIPTION OF ILLUSTRATIVE EMBODIMENTS

Figure 1:
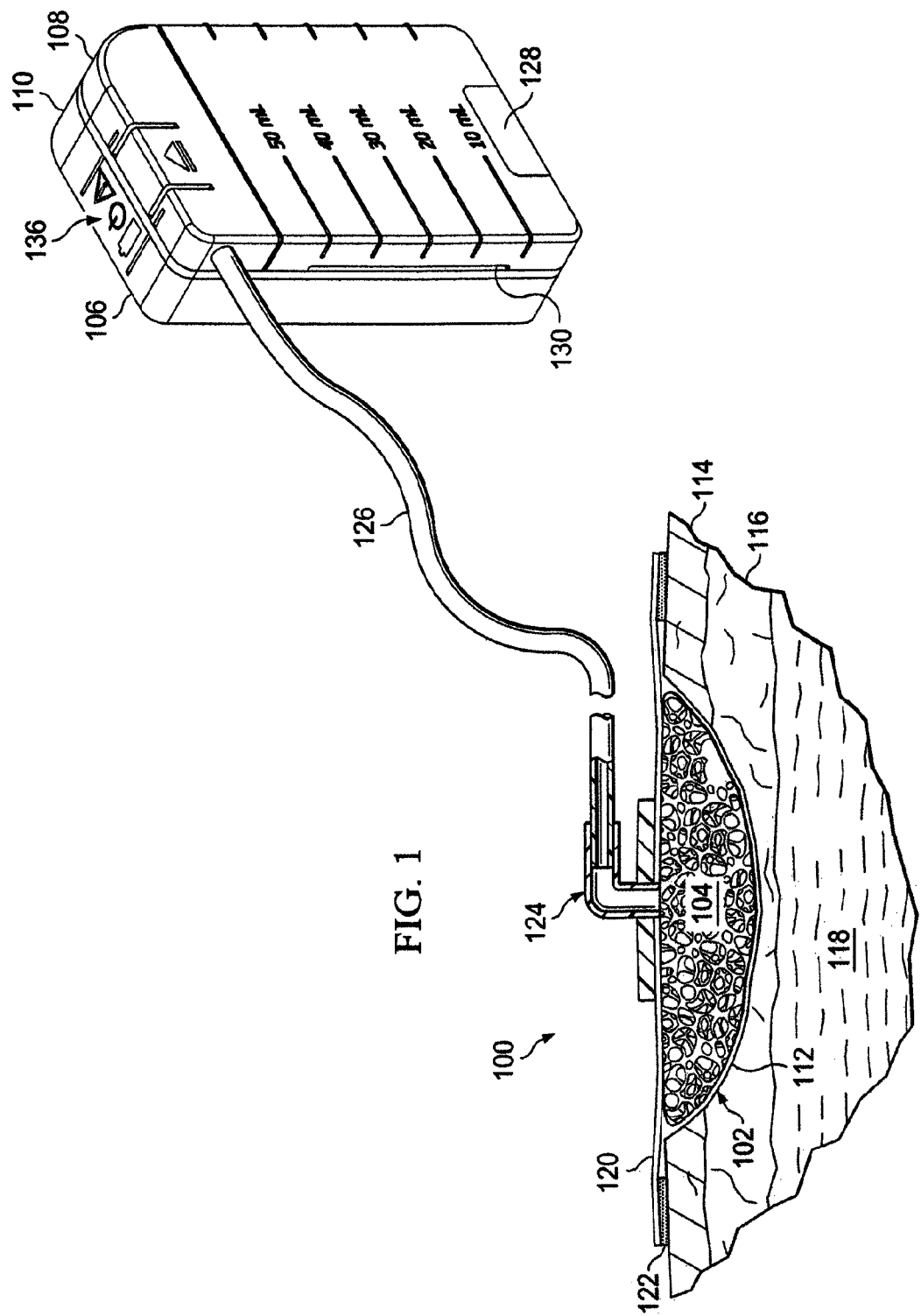
FIG. 1 is a schematic diagram, with a portion shown in cross section and a portion shown in perspective, of an illustrative, non-limiting embodiment of a reduced-pressure treatment system.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Referring to the drawings and initially to FIGS. 1-4, an illustrative, non-limiting embodiment of a reduced-pressure treatment system 100 for providing reduced-pressure treatment to a tissue site 102 of a patient is presented. The reduced-pressure treatment system 100 includes a manifold 104 placed proximate to the tissue site 102. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. In this embodiment, the tissue site 102 includes tissue in a body cavity, and in particular the abdominal cavity, and includes the abdominal contents or tissue proximate the abdominal contents. Treatment of tissue site 102 may include removal of fluids, e.g., ascites, protection of the abdominal cavity, or delivery of reduced pressure.

A reduced-pressure treatment device 106 that is fluidly coupled to the manifold 104. The reduced-pressure treatment device 106 has a canister unit 108 and a pump control unit 110. The pump control unit 110 is fluidly separate or isolated from the canister unit 108. Fluidly separating the pump control unit 110 and the canister unit 108 helps prevent the pump control unit 110 from being contaminated by fluids. Separating the pump control unit 110 and the canister unit 108 also facilitates reusing high-value components of the pump control unit 110. Moreover, the separation may, in some embodiments, facilitate making the canister unit 108 disposable. The pump control unit 110 and the canister unit 108 are further described below.

The reduced-pressure treatment system 100 is used to treat the tissue site 102, which may be a wound 112. In one illustrative, non-limiting embodiment, the wound 112 is through or involves epidermis 114, dermis 116, and subcutaneous tissue 118. The reduced-pressure treatment system 100 may also be used at other tissue sites. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity.

The manifold 104 is disposed proximate to the tissue site 102. A manifold is a substance or structure that is provided to assist in applying reduced pressure to, delivering fluids to, or removing fluids from a tissue site 102. The manifold 104 typically includes a plurality of flow channels or pathways that distribute fluids provided to and removed from the tissue site 102 around the manifold 104. In one illustrative embodiment, the flow channels or pathways are interconnected to improve distribution of fluids provided or removed from the tissue site 102. The manifold 104 may be a biocompatible material that is capable of being placed in contact with tissue site 102 and distributing reduced pressure to the tissue site 102. Examples of manifolds 104 may include, for example, without limitation, devices that have structural elements arranged to form flow channels, such as, for example, cellular foam, open-cell foam, porous tissue collections, liquids, gels, and foams that include, or cure to include, flow channels. The manifold 104 may be porous and may be made from foam, gauze, felted mat, or any other material suited to a particular biological application. In one embodiment, the manifold 104 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the manifold 104 may also be used to distribute fluids such as medications, antibacterials, growth factors, and various solutions to the tissue site 102. Other layers may be included in or on the manifold 104, such as absorptive materials, wicking materials, hydrophobic materials, and hydrophilic materials.

In one embodiment, the manifold 104 may be constructed from bioresorbable materials that do not have to be removed from a patient's body following use of the reduced-pressure dressing. Suitable bioresorbable materials may include, without limitation, a polymeric blend of polylactic acid (PLA) and polyglycolic acid (PGA). The polymeric blend may also include without limitation polycarbonates, polyfumarates, and capralactones. The manifold 104 may further serve as a scaffold for new cell-growth, or a scaffold material may be used in conjunction with the manifold 104 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

A sealing member 120 is placed over the manifold 104 and a portion of the patient's epidermis 114. The sealing member 120 may be an elastomeric material or any material or substance that provides a fluid seal. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further still, the sealing member 120 may include a silicone drape, 3M Tegaderm® drape, acrylic drape such as one available from Avery Dennison.

The sealing member 120 may have an attachment device 122 that helps form a fluid seal between the sealing member 120 and the patient's epidermis 114. The attachment device 122 may be used to hold the sealing member 120 against the patient's epidermis 114 or another layer, such as a gasket or additional sealing member. The attachment device 122 may take numerous forms. For example, the attachment device 122 may be a medically acceptable, pressure-sensitive adhesive or a hydrocolloid that extends about a periphery of the sealing member 120. The fluid seal is adequate to maintain reduced pressure at a desired site given the particular reduced-pressure source or subsystem involved.

A reduced-pressure interface 124 may be coupled to the sealing member 120 to provide fluid access to the manifold 104. A reduced-pressure delivery conduit 126 fluidly couples the reduced-pressure treatment device 106 and the reduced-pressure interface 124. In one illustrative embodiment, the reduced-pressure interface 124 is a T.R.A.C.® Pad or Sensa T.R.A.C.® Pad available from KCI of San Antonio, Tex. The reduced-pressure interface 124 allows the reduced pressure to be delivered to the tissue site 102. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

Reduced pressure is a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold 104, the reduced-pressure delivery conduit 126, and proximate the tissue site 102. As the hydrostatic pressure around the tissue site 102 approaches the desired reduced pressure, the flow may subside, and the reduced pressure may be maintained. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site 102 may be more than the pressure normally associated with a complete vacuum. Consistent with the use herein, an increase in reduced pressure or vacuum pressure refers to a relative reduction in absolute pressure.

The reduced-pressure treatment device 106 delivers reduced pressure and receives fluids, such as exudates, from the tissue site 102. The reduced-pressure treatment device 106 includes an attaching device, such as clip member 128, to hold the canister unit 108 proximate to the pump control unit 110. The attaching device or clip member 128 in the embodiment shown may hold the canister unit 108 substantially flush against the pump control unit 110. An air gap channel 130 may be formed between the canister unit 108 and the pump control unit 110. A front portion 132 of the canister unit 108 may be transparent to allow fluid within the canister unit 108 to be viewed from outside of the canister unit 108. A graduated scale 134 may be included on the front portion 132 to visually determine the amount of liquids in the canister unit 108. The reduced-pressure delivery conduit 126 fluidly couples to the canister unit 108 to deliver reduced pressure to the tissue site 102 and to deliver fluids from the tissue site 102 to the canister unit 108.

Figure 2:
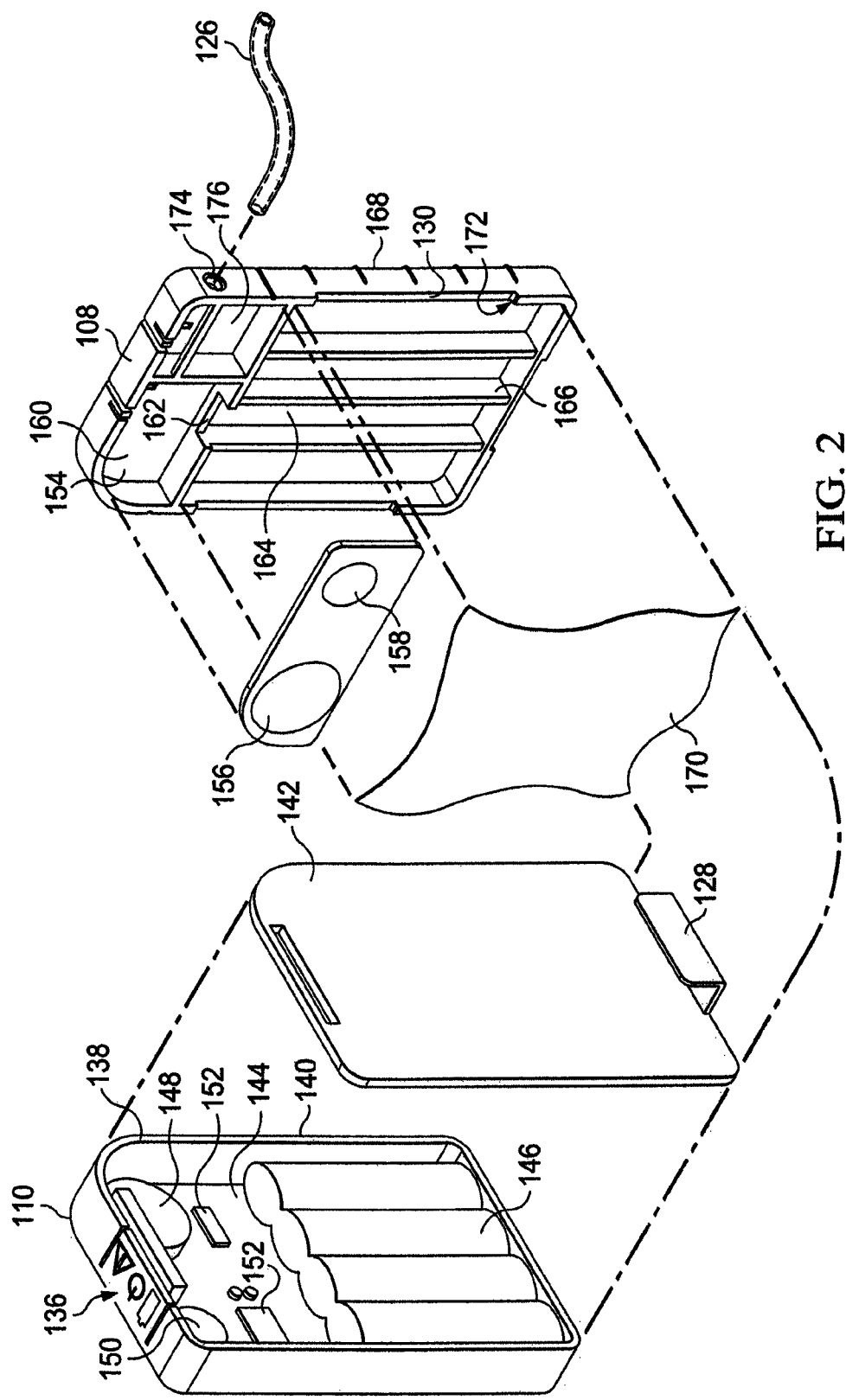
FIG. 2 is a schematic, exploded, perspective view of an illustrative, non-limiting embodiment of a reduced-pressure treatment device.

Referring now primarily to FIG. 2, an exploded view of the reduced-pressure treatment device 106 is presented. The pump control unit 110 may include a pump control unit housing 138 that may include a base portion 140 and a cover 142. An interior 144 of the base portion 140 may include batteries 146, or power unit, or other power supply. In one embodiment, the batteries 146 may be recharged by placing the reduced-pressure treatment device 106 on a charging cradle (not shown). The interior 144 may also include a first electromagnet 148 and a second electromagnet 150. The electromagnets 148, 150 may be, for example, electromagnetic coils or solenoids. A control device 152 is included within the interior 144 and provides controlling elements for the electromagnets 148, 150. The control device 152 may also execute inputs from a user interface device 136 as described below. The cover 142 is sized and configured to mate with the base portion 140 and provide a substantially fluid tight seal therewith. The cover 142 may be removeably or permanently joined to the base portion 140 by welding, fasteners, or other coupling techniques.

The pump control unit 110 is configured to be secure in close proximity to the canister unit 108. In the illustrative embodiment, the canister unit 108 is made to be placed inside of the clip member 128 and form an interference fit to hold the canister unit 108 against the pump control unit 110. It should be understood that numerous other techniques and devices may be used for holding the pump control unit 110 in close proximity to the canister unit 108.

The canister unit 108 includes a pump head 154. The pump head 154 may include one or more diaphragms, such as a first diaphragm 156 and a second diaphragm 158. The diaphragm includes a sheet of semi-flexible or flexible material anchored at the sheet's periphery to a wall. The pump head 154 may further include a pump chamber 160. The pump head 154 is operable to produce a reduced pressure that is delivered through a conduit or aperture 162 to a fluid reservoir 164, which may include one or more baffles 166. The canister unit 108 has a base portion 168 and a membrane 170. The membrane 170 may be vapor permeable. The membrane 170 covers at least a portion of the fluid reservoir 164 and may be supported in part by the baffles 166. The base portion 168 of the canister unit 108 includes a recessed portion 172 that forms the air gap channel 130 between the canister unit 108 and the pump control unit 110 when assembled. The membrane 170 may be an ultra high moisture-vapor transmission ratio (MVTR) membrane that allows water vapor to pass from the fluid reservoir 164 to atmosphere. The air gap channel 130 facilitates the transfer of the water vapor.

The reduced-pressure delivery conduit 126 interfaces with a reduced-pressure inlet 174 and delivers fluids to a receiving chamber 176 that is in fluid communication with the pump chamber 160. The second electromagnet 150 may be a second pressure detector that may monitor the level of reduced pressure in the reduced-pressure delivery conduit 126, and consequently, the tissue site 102, by measuring the position of the second diaphragm 158. The position of the second diaphragm 158 is measured via the change in inductance experienced by the second electromagnet 150 as the second diaphragm 158 is displaced. Likewise, the first electromagnet 148 may include a first pressure detector (not shown) that may measure the pressure in the canister unit 108 by measuring the position of the first diaphragm 156 via the change in inductance experienced by the first electromagnet 148 as the first diaphragm 156 moves.

Figure 4:
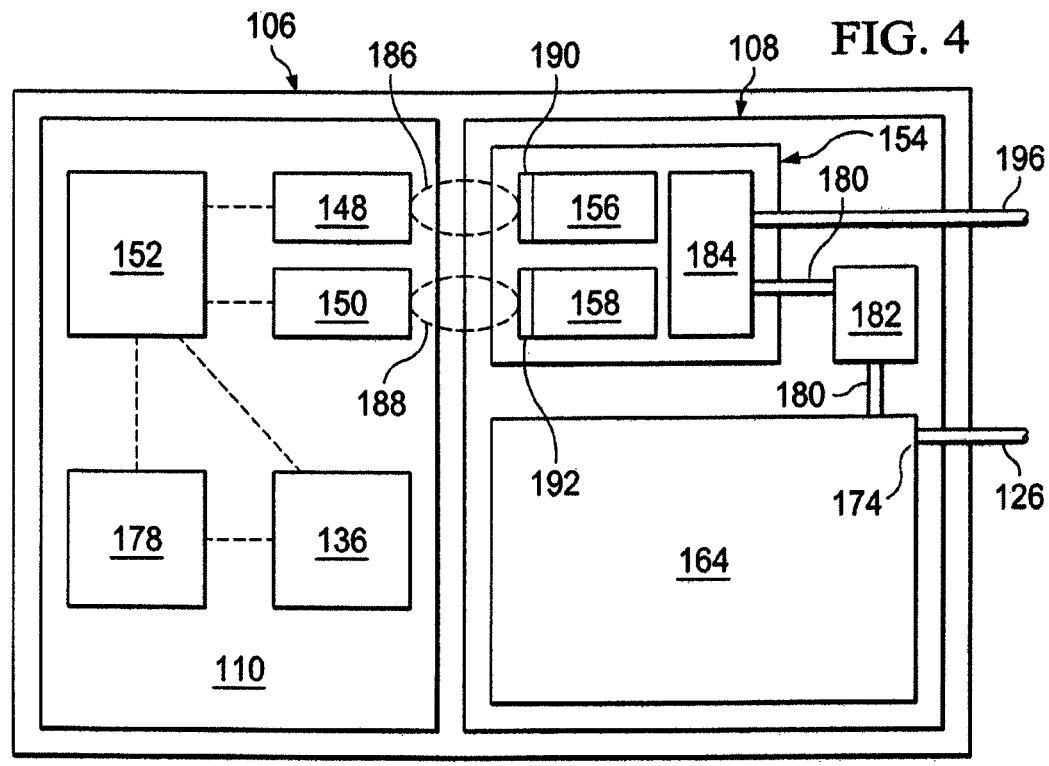
FIG. 4 is a schematic diagram of an illustrative, non-limiting embodiment of a reduced-pressure treatment device.

Referring now primarily to FIG. 4, the reduced-pressure treatment device 106 includes the canister unit 108 and the pump control unit 110. The pump control unit 110 is fluidly separate or isolated from the pump head 154. The pump control unit 110 is also fluidly separate from the canister unit 108. The pump control unit 110 communicates or provides pump energy to the pump head 154. The pump energy in turn moves components, e.g., the first diaphragm 156, on the pump head 154 and that movement is used to generate reduced pressure. In some embodiments, the second diaphragm 158 may be included in the pump head 154 to generate reduced pressure or to measure the reduced pressure.

A valve assembly 184 may be associated with the first diaphragm 156 and the pump chamber 160 (FIG. 2). The valve assembly 184 may be, for example, one or more one-way valves (see, e.g., one-way valves 194 in FIG. 5A) that allow fluids to be moved out of the pump chamber 160 to produce a reduced pressure that is communicated to conduit 180. Other techniques for using moving components to produce reduced pressure may be used.

The pump control unit 110 may include the user interface device 136, the control device 152, and a power subsystem 178, such as the batteries 146 (FIG. 2). The pump control unit 110 may be configured for one setting of operation, and in such an illustrative embodiment, power from the power subsystem 178 may be supplied directly to the control device 152. The reduced-pressure treatment device 106 will then produce reduced pressure at the pre-set level.

In another illustrative embodiment, a user may enter parameters into the reduced-pressure treatment device 106, such as a desired pressure range, time duration for operation, or other performance parameters. In this latter illustrative embodiment, the user interface device 136 may be used. The user interface device 136 may be a panel with selector buttons for input as well as a display for presenting information and options to the user. The user interface device 136 may be electrically coupled to the power subsystem 178 and to the control device 152.

The user interface device 136 takes user interaction and translates that into an electrical or software code command for use in the reduced-pressure treatment device 106. The user interface device 136 may be a capacitive or resistive touch panel over (or with) LCD, OLED, or LED screens; membrane panels with buttons and LEDs; enclosure mounted buttons with LEDs; enclosure-mounted capacitive sensors; gesture recognition cameras; or combinations of the aforementioned technologies. In one illustrative, non-limiting embodiment, the user interface device 136 is a basic switch that requires no decoding to determine the command which can be passed onto the control device 152. In another illustrative embodiment, the user interface device 136 is a touch screen and LCD combination that requires a software code to determine the user command. Generally, the user interface device 136 determines and communicates the command from a user to the control device 152, and may send feedback to the user regarding the status of treatment from the control device 152 or module.

The control device 152 controls the treatment administered with the reduced-pressure treatment system 100 and, in this illustrative embodiment, controls the action of the linking interfaces 186, 188 based upon commands from the user via the user interface device 136. The control device 152 translates the power provided by the power subsystem 178 into the pump energy for a first linking interface 186 and a second linking interface 188 as will be described further below and may sequence the linking interfaces 186, 188. In some illustrative embodiments, the control device 152 contains control electronics, such as a microprocessor running therapy code and drive electronics capable of controlling the linking interfaces 186, 188. The power for the control device 152 is derived from the power subsystem 178, which provides power to the reduced-pressure treatment system 100 at the appropriate levels to drive the control device 152 and the linking interfaces 186, 188.

The power subsystem 178 may communicate data and power to the control device 152 and to the user interface device 136. The power subsystem 178 provides the appropriate power for the control device 152 and the user interface device 136 and may provide status information, which can be monitored by the control device 152. The status information may include whether the power subsystem 178 is connected to main power and the status of the battery charge. The status information may be presented to the user via the user interface device 136. The power subsystem 178 also may charge the battery and switch over to the battery if the main power connection is disconnected.

The canister unit 108 includes the fluid reservoir 164 and the pump head 154. In this illustrative embodiment, the reduced-pressure delivery conduit 126 delivers fluids to the fluid reservoir 164 through the reduced-pressure inlet 174. The pump head 154 develops reduced pressure when the pump head 154 receives pump energy. The reduced pressure is delivered through the conduit 180 to the fluid reservoir 164. The conduit 180 may include one or more filters 182, such as a hydrophobic filter, to prevent liquids from contaminating the pump head 154. The canister unit 108 may further include a vent conduit 196 that vents gas from the wound 112 (FIG. 1) to an exterior of the reduced-pressure treatment device 106.

In operation, pump energy is supplied to the pump head 154 by at least one linking interface, such as the first linking interface 186. In this illustrative embodiment, the first linking interface 186 includes the first electromagnet 148 and a first magnetic member 190 associated with the first diaphragm 156. The first magnetic member 190 may be a metal washer or other member coupled to the first diaphragm 156.

In some embodiments, the user activates the reduced-pressure treatment device 106 using the user interface device 136. The control device 152 activates the first electromagnet 148 to develop an alternating magnetic field that is magnetically coupled to the first magnetic member 190 on the first diaphragm 156. The first electromagnet 148 may create an electromagnetic field in a direction substantially aligned with the location of the first diaphragm 156. The movement of the first diaphragm 156 in conjunction with the valve assembly 184 allows for the production of reduced pressure that is delivered into the conduit 180 and to the fluid reservoir 164. The reduced pressure then communicates through the reduced-pressure delivery conduit 126 to the tissue site 102. It should be appreciated that the first linking interface 186 allows pump energy to be delivered to the pump head 154 without any fluid communication between the pump head 154 and the canister unit 108. Accordingly, contaminants in the canister unit 108—whether gaseous or liquid—cannot reach the pump control unit 110. The more highly-valued components may reside in the pump control unit 110 and are protected from contamination. In one embodiment, the canister unit 108 may be disposable such that fresh canister units may be used with the same pump control unit 110 for ongoing applications.

In some embodiments, the second diaphragm 158 may be used with the second linking interface 188 to generate reduced pressure. The second diaphragm 158 has a second magnetic member 192 and works with the second linking interface 188 in a manner analogous to the first diaphragm 156 and the first linking interface 186. In another embodiment, the second diaphragm 158 may be provided to measure the pressure within the pump head 154.

In this latter embodiment, the displacement of the second diaphragm 158, and particularly the second magnetic member 192, is sensed via the change in induction experienced by the second electromagnet 150. Other techniques may be used for detecting displacement of the second diaphragm 158. For example, the pump control unit 110 may include an infrared sensor that sends an infrared signal onto the second diaphragm 158, and particularly, without limitation, onto the face where the magnetic member 192 is or otherwise would be. The infrared signal returns to the infrared sensor and the distance can be detected and the displacement ascertained. In another example, the pump control unit 110 may include a capacitance sensor and the second diaphragm 158 may include a plate that when moved changes the capacitance detected by the capacitance sensor on the pump control unit 110. In another embodiment, a ferrite material may be coupled to the second diaphragm 158. A Hall Effect sensor in the pump control unit 110 may be used to sense a change in flux due to movement of the ferrite that allows the displacement to be sensed.

In another embodiment, in addition to or in lieu of measuring displacement of the second diaphragm 158, the pump control unit 110 may have a sensor for determining displacement of the first diaphragm 156 using analogous techniques. In this latter embodiment, the reduced-pressure treatment device 106 may stop providing pump energy to the first diaphragm 156 such that the reduced pressure in the pump head 154 acts on the first diaphragm 156. The sensor may then measure the displacement of the first diaphragm 156. The pressure in the pump head 154 may be determined using the displacement measurement. When both diaphragms 156, 158 are used to measure reduced pressure, one diaphragm may be used to measure the pressure in the pump head 154 and the other diaphragm used to measure pressure at another location such as in a sampling conduit (not shown). The sampling conduit may be associated with the reduced-pressure delivery conduit 126.

Figure 5C:
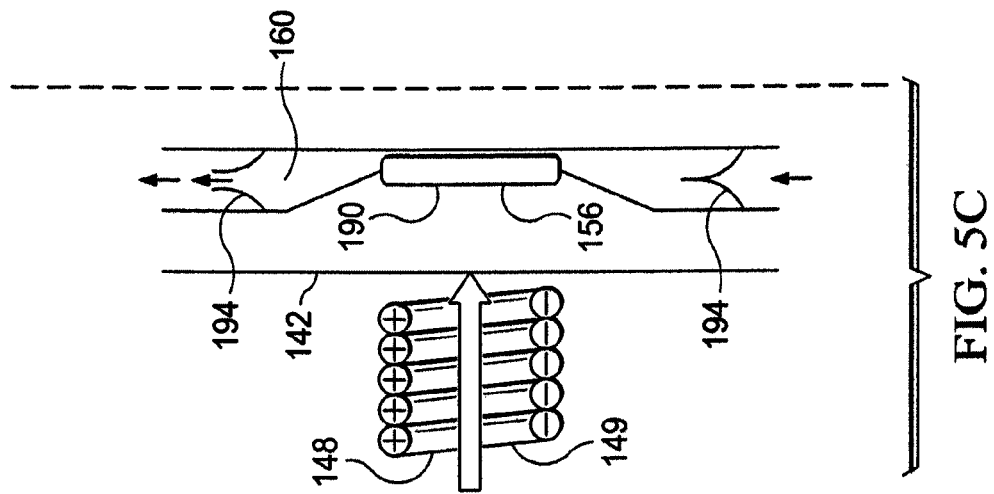
FIGS. 5A-5C are schematic diagrams showing an illustrative, non-limiting embodiment of a linking interface and showing a portion of a pump head in different positions involved with pumping.
Figure 5B:
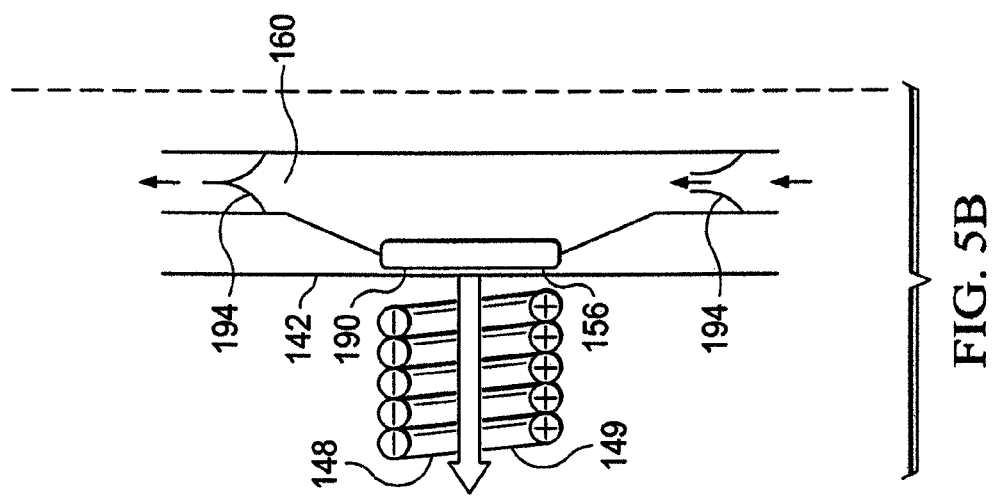
Figure 5A:
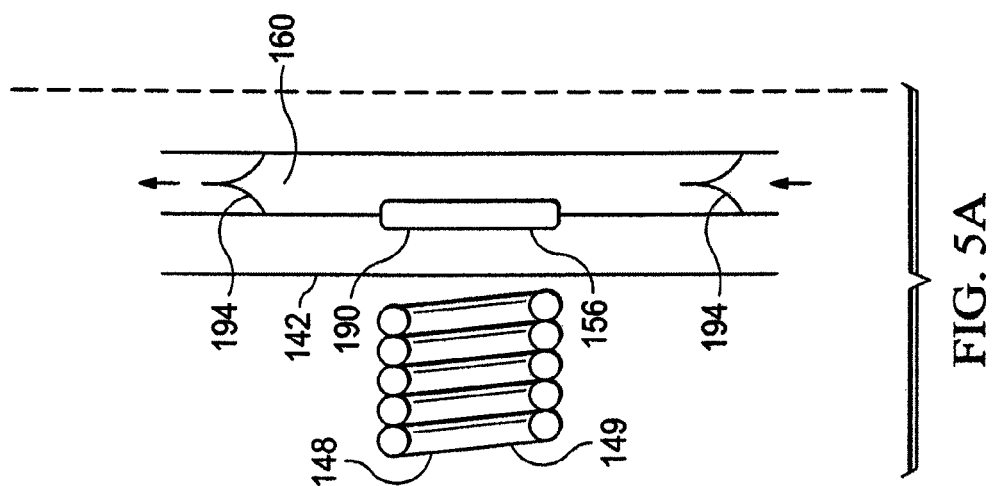

Referring now primarily to FIGS. 5A-5C, a diagram is presented illustrating how the first electromagnet 148, which may be a magnetic coil 149, interacts with the first magnetic member 190 on the first diaphragm 156 and the pump chamber 160 to produce reduced pressure. The first electromagnet 148 may be within the interior 144 (FIG. 2) of the base portion 140 (FIG. 2) and may have the cover 142 disposed between the first electromagnet 148 and the first diaphragm 156. FIG. 5A shows the first electromagnet 148 in the un-energized position, or neutral position. In FIG. 5B, the first electromagnet 148 has been energized and provides an electromagnetic force that acts on the first magnetic member 190. As such, the electromagnetic force urges the first magnetic member 190 towards the first electromagnet 148 to a first position. FIG. 5C shows the electromagnetic force having been reversed such that the first electromagnet 148 urges the first magnetic member 190 away from the first electromagnet 148 to a second position. It should be appreciated that the volume ($V_1$) of the pump chamber 160 in the first position is greater than the volume ($V_2$) in the second position. Thus, fluid in the pump chamber 160 is removed and then, as the first magnetic member 190 is urged back towards the first electromagnet 148, a reduced pressure is created within the pump chamber 160. The reduced pressure remains in the pump chamber 160 because fluid is not pulled back into the pump chamber 160 because of the one-way valves 194.

Referring again primarily to FIG. 1, in operation of the reduced-pressure treatment system 100, the manifold 104 is disposed proximate the tissue site 102. The manifold 104 and a portion of the patient's epidermis 114 are covered with sealing member 120. The sealing member 120 is used to help form a fluid seal over the manifold 104 and the tissue site 102. If not already installed, the reduced-pressure interface 124 is installed to provide fluid access to the manifold 104. The reduced-pressure delivery conduit 126 is used to fluidly couple the reduced-pressure interface 124 to the reduced-pressure treatment device 106.

Then the reduced-pressure treatment device 106 is activated. In some embodiments, the reduced-pressure treatment device 106 may be activated using the user interface device 136. As previously described, activation of the reduced-pressure treatment device 106 energizes the first linking interface 186 and provides pump energy from the pump control unit 110 to the pump head 154. The second linking interface 188 may also provide pump energy from the pump control unit 110 to the pump head 154 and particularly the second diaphragm 158. The pump energy moves at least one diaphragm, e.g., the first diaphragm 156, and develops reduced pressure as previously described. Throughout the operation or at intervals the pressure in the pump head 154 or at the tissue site 102 may be determined by sensing displacement of the diaphragms 156, 158 as previously described.

Figure 6:
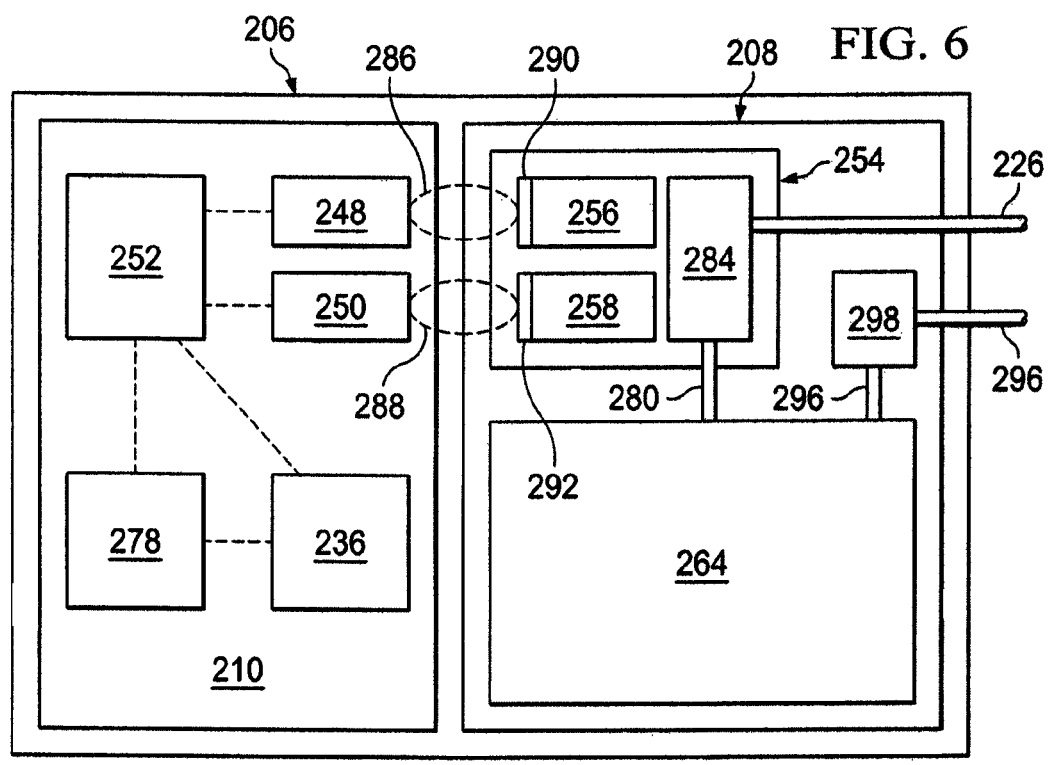
FIG. 6 is a schematic diagram of an illustrative reduced-pressure treatment device showing a pump head acting directly on fluid received from a tissue site.

Referring now primarily to FIG. 6, another illustrative, non-limiting embodiment of a reduced-pressure treatment device 206 is presented. The reduced-pressure treatment device 206 is analogous to the reduced-pressure treatment device 106 of FIG. 4 except that a pump head 254 operates on fluids directly returning from a reduced-pressure delivery conduit 226 that are then delivered by a conduit 280 to a fluid reservoir 264. As in the embodiment of FIG. 4, the reduced-pressure treatment device 206 includes a pump control unit 210 and a canister unit 208. The pump control unit 210 may include controls or a user interface device 236, a power subsystem 278, a control device 252, a first electromagnet 248, and a second electromagnet 250 that are analogous to the user interface device 136, the power subsystem 178, the control device 152, the first electromagnet 148, and the second electromagnet 150, respectively, of FIG. 4.

The canister unit 208 includes the pump head 254. The pump head 254 includes a first diaphragm 256 and a second diaphragm 258 that may have a first magnetic member 290 and a second magnetic member 292, respectively. The pump head 254 may include a valve assembly 284 that operates in conjunction with the first diaphragm 256 to produce reduced pressure. The first diaphragm 256 acts directly on fluids delivered from the reduced-pressure delivery conduit 226. The canister unit 208 may further include a vent conduit 296 that vents gas from the wound, e.g. the wound 112 of FIG. 1, to an exterior of the reduced-pressure treatment device 206. A filter 298 may be added to the vent conduit 296 to prevent liquids and odor from exiting the canister unit 208.

In operation, pump energy is supplied from the first electromagnet 248 to the first diaphragm 256 by a first linking interface 286. The pump energy moves the first diaphragm 256 and creates reduced pressure. The first linking interface 286 includes the first electromagnet 248 and the first magnetic member 290 on the first diaphragm 256. The first linking interface 286 may further monitor pressure in the canister unit 208 by sensing displacement as previously described. Similarly, a second linking interface 288 includes the second electromagnet 250 and the second magnetic member 292 on the second diaphragm 258 for monitoring pressure at the tissue site 102, e.g., the wound 112 of FIG. 1.

Referring still primarily to FIG. 6, but in regard to an alternative illustrative embodiment, the linking interfaces 286, 288 may be a mechanical link. In this illustrative embodiment, the first linking interface 286 may include the first electromagnet 248, a first mechanical actuator (not explicitly shown), and the first diaphragm 256. The first electromagnet 248 receives a first end (proximal end) of a first mechanical actuator (not explicitly shown) and the first diaphragm 256 receives a second, opposing end (distal end) of the first mechanical actuator. When energized, the first electromagnet 248 moves the first mechanical actuator, and the first mechanical actuator in turn moves the first diaphragm 256. The first electromagnet 248 may monitor the pressure in the canister unit 208 by measuring the position of the first diaphragm 256. Similarly, the second linking interface 288 may include the second electromagnet 250, a second mechanical actuator (not explicitly shown), and the second diaphragm 258. The second linking interface 288 may move the second diaphragm 258 to produce reduced pressure. In addition or alternatively, the second electromagnet 250 may monitor the pressure level in the reduced-pressure delivery conduit 226 by measuring the position of the second diaphragm 258 via the second mechanical actuator. The first and second mechanical actuators may optionally include hydraulic fluids. Thus, the first and second linking interfaces 286, 288 operate to move the first and second diaphragms 256, 258, respectively, while remaining fluidly isolated from any of the fluid paths within the canister unit 208.

Figure 7:
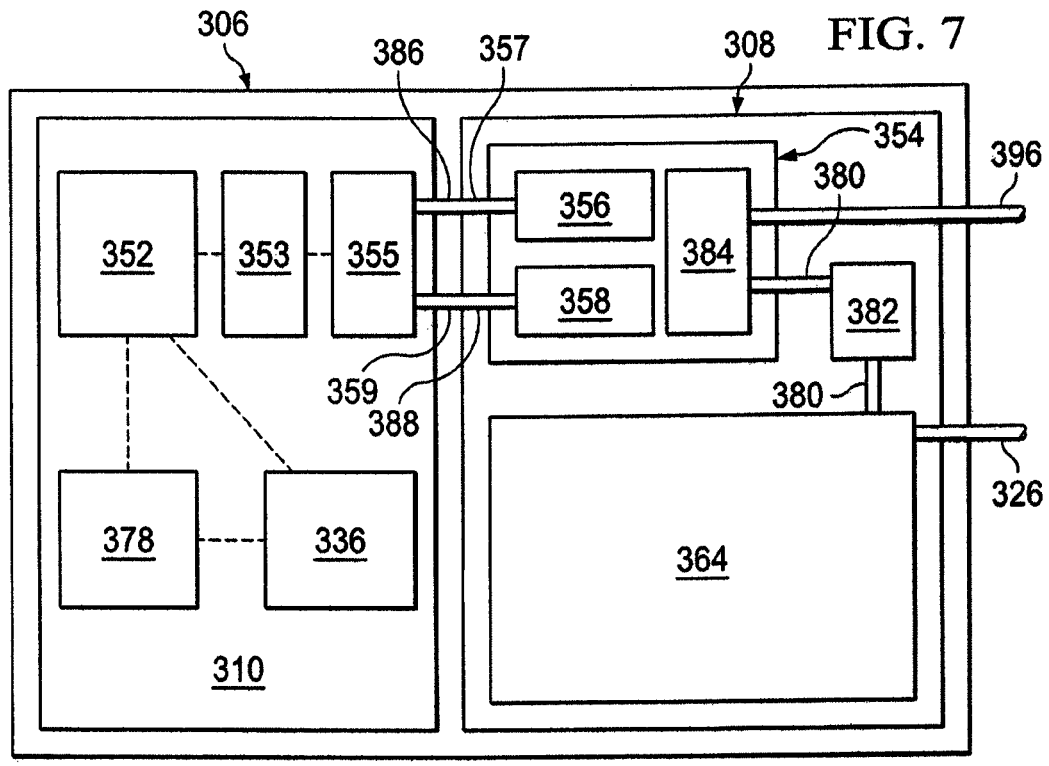
FIG. 7 is a schematic diagram of another illustrative, non-limiting embodiment of a reduced-pressure treatment device.

Referring now primarily to FIG. 7, another illustrative, non-limiting embodiment of a reduced-pressure treatment device 306 is presented. The reduced-pressure treatment device 306 is analogous in most respects to the reduced-pressure treatment device 106 in FIG. 4. For example, the reduced-pressure treatment device 306 includes a canister unit 308 and a pump control unit 310. The pump control unit 310 may include controls or a user interface device 336, which is analogous to the user interface device 136 of FIG. 2. The pump control unit 310 further includes a power subsystem 378. The power subsystem 378 and the user interface device 336 may be electronically coupled to a control device 352. In this illustrative embodiment, the pump control unit 310 further includes a first pump 353 and may further include a valve assembly 355. The first pump 353, alone or in conjunction with the valve assembly 355, provides positive or reduced pressure through a first conduit 357 to a first diaphragm 356 in order to cause the first diaphragm 356 to move. Similarly, a second conduit 359 may provide positive or reduced pressure to a second diaphragm 358.

The canister unit 308 includes a pump head 354, or second pump, that includes the first and second diaphragms 356, 358. A second valve assembly 384 may be included with the pump head 354. The first diaphragm 356, alone or with the second valve assembly 384, operates under the influence of pump energy to produce reduced pressure that is delivered to a conduit 380 and subsequently to a fluid reservoir 364. The conduit 380 may include one or more filters 382, such as a hydrophobic filter. The reduced pressure in the fluid reservoir 364 is delivered to a reduced-pressure delivery conduit 326. The canister unit 308 may further include a vent conduit 396 that vents gas from the tissue site, such as the wound 112 of FIG. 1, to an exterior of the reduced-pressure treatment device 306.

In the reduced-pressure treatment device 306, the first conduit 357 forms a portion of a first linking interface 386. The first linking interface 386 further includes the first pump 353 (and optionally the valve assembly 355) and the first diaphragm 356. The first linking interface 386 may include a first pressure detector (not shown). Thus, positive pressure or reduced pressure generated by the first pump 353 is communicated to the first diaphragm 356 and constitutes pump energy that may be used to develop reduced pressure in the pump head 354. Pressure within the canister unit 308 may be monitored using the first pressure detector (not shown) by measuring the position of the first diaphragm 356. Similarly, the second conduit 359 makes up a portion of a second linking interface 388. The second linking interface 388 also includes the first pump 353 (and optionally the valve assembly 355), the second diaphragm 358, and a second pressure detector (not shown). Pressure at the wound, e.g., the wound 112 of FIG. 1, may be monitored using the second pressure detector (not shown) by measuring the position of the second diaphragm 358.

The first and second linking interfaces 386 and 388, provide a pneumatic coupling between the pump control unit 310 and the canister unit 308. The first pump 353 may be run at a constant load point and may further include a reservoir between the first pump 353 and the valve assembly 355. The first pump 353 can switch back and forth between ambient and higher pressure. In an alternative illustrative embodiment, the first pump 353 may be replaced with a compressed gas vessel and a compressed gas may be provided to the first diaphragm 356 to provide the pump energy to develop reduced pressure in the pump head 354. (It should be noted that the first conduit 357 provides pump energy to the pump head 354, but remains fluidly isolated from the contaminated fluid paths of the canister unit 308.)

Figure 8:
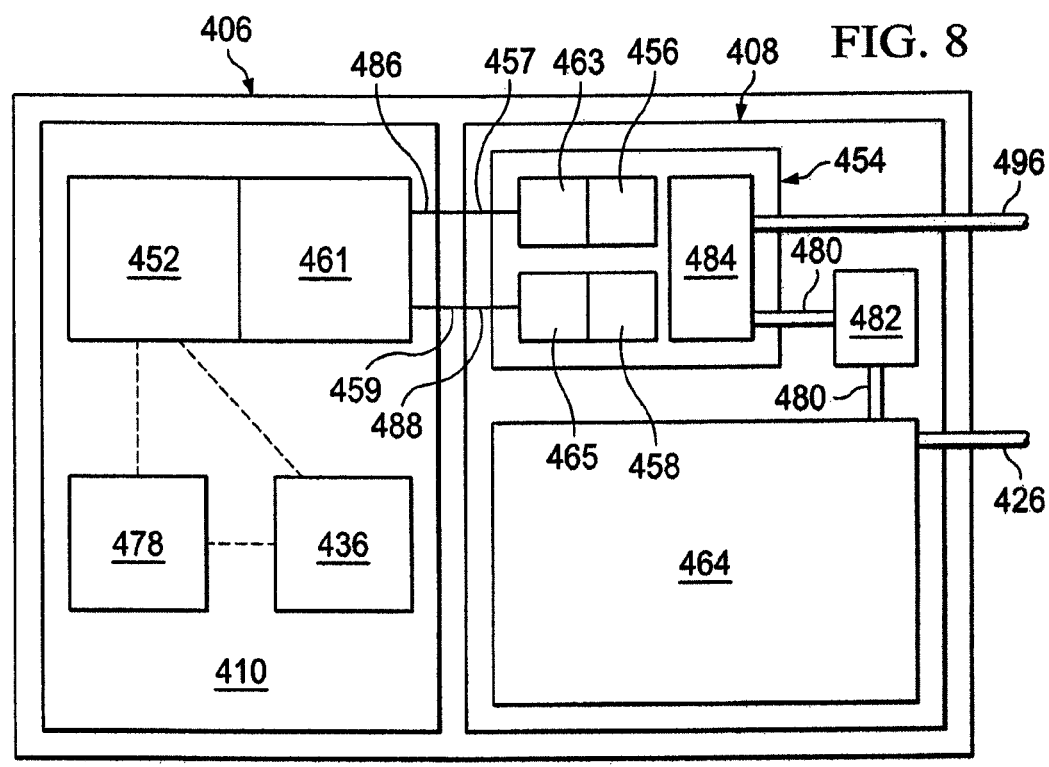
FIG. 8 is a schematic diagram of still another illustrative, non-limiting embodiment of a reduced-pressure treatment device.

Referring now primarily to FIG. 8, another illustrative, non-limiting embodiment of a reduced-pressure treatment device 406 that is analogous in most respects to the reduced-pressure treatment device 106 of FIGS. 1-6 is presented. The reduced-pressure treatment device 406 includes a canister unit 408 and a pump control unit 410. The pump control unit 410 may include controls or a user interface device 436, a power subsystem 478, and a control device 452. As before, the user enters data or desired settings on the user interface device 436. The power subsystem 478 provides power to the control device 452. In this illustrative embodiment, the control device 452 further includes a piezoelectric controller and driver unit 461.

The piezoelectric controller and driver unit 461 is electrically coupled by a first electrical coupling 457 to a first piezoelectric member 463, which is part of or coupled to a first diaphragm 456. Similarly, a second electrical conduit 459 couples the piezoelectric controller and driver unit 461 to a second piezoelectric member 465, which is part of or coupled to second diaphragm 458. Thus, a first linking interface 486 includes the piezoelectric controller and driver unit 461, the first electrical coupling 457, a first pressure detector (not shown), and the first piezoelectric member 463. Pump energy may be delivered through the first linking interface 486 to the first diaphragm 456. Pressure within the canister unit 408 may further be monitored by measuring the position of the first diaphragm 456 using the first pressure detector (not shown). A second linking interface 488 includes the piezoelectric controller and driver unit 461, the second electrical coupling 459, a second pressure detector (not shown), and the second piezoelectric member 465. Pressure in a reduced-pressure delivery conduit 426 may be monitored by the piezoelectric controller and driver unit 461 by measuring the position of the second diaphragm 458, via the second pressure detector (not shown). The first diaphragm 456 works within a pump head 454 to produce reduced pressure that is delivered by a conduit 480 to a fluid reservoir 464. The conduit 480 may include one or more filters 482, such as a hydrophobic filter. The reduced pressure delivered into the fluid reservoir 464 communicates reduced pressure to the reduced-pressure delivery conduit 426.

In operation, the control device 452 and the piezoelectric controller and driver unit 461 provide a first piezoelectric control signal that is delivered by the first electrical coupling 457 to the first piezoelectric member 463. The first piezoelectric member 463, when energized, causes movement of the first diaphragm 456. The movement of the first diaphragm 456 and the pump head 454 develops reduced pressure that is delivered to the conduit 480. A valve assembly 484 may be included within the pump head 454 to help produce the reduced pressure. The canister unit 408 may further include a vent conduit 496 that vents gas from a wound, such as the wound 112 of FIG. 1, to an exterior of the reduced-pressure treatment device 406.

In another illustrative, non-limiting embodiment (not shown) that is analogous in most respects to the reduced-pressure treatment device 106 of FIGS. 1-4, a reduced-pressure treatment device is presented that includes a pump control unit and a canister unit. The pump control unit may include a user interface device, a power subsystem, and a control device. The user interface device and the power subsystem may be electronically coupled to the control device. The pump control unit may further include one or more laser lights. The canister unit includes a pump head that may have one or more diaphragms that correspond to the one or more laser lights. In operation, pump energy is supplied to the one or more diaphragms by one or more linking interfaces.

In this embodiment, the linking interface include the laser light and the diaphragm. The linking interface is operable to deform the diaphragm via laser light to create a pumping action within the pump head to generate reduced pressure. In this illustrative embodiment, the one or more diaphragms may be thermo-reactive diaphragms that may be made from spectra-absorbent polymers that absorb light and which are treated with conductive materials that may help dissipate heat generated by the laser light. The thermo-reactive diaphragms are operable to deform under the application of laser light. In another illustrative embodiment, the one or more diaphragms may be made from a flexible material capable of absorbing a defined wavelength of light to undergo a change in crystalline morphology that changes the density of the material thereby changing the shape of the diaphragm; i.e., the flexible material is operable to deform under the application of laser light.

In view of the foregoing illustrative, non-limiting embodiments of FIGS. 1-8, it should be clear that a linking interface is any arrangement for providing energy from the pump control unit to the pump head while keeping the pump control unit fluidly separate or isolated from the potentially contaminated portion of the pump head. In many instances, the linking interface involves using a magnetic field. Other embodiments of the linking interface include using a pneumatic link that moves the diaphragm, using a mechanical actuator that goes between the pump control unit and pump head (on an isolated side of the diaphragm), using laser light as presented in the previous paragraph, and using a piezoelectric member to move the diaphragm.

Figure 9:
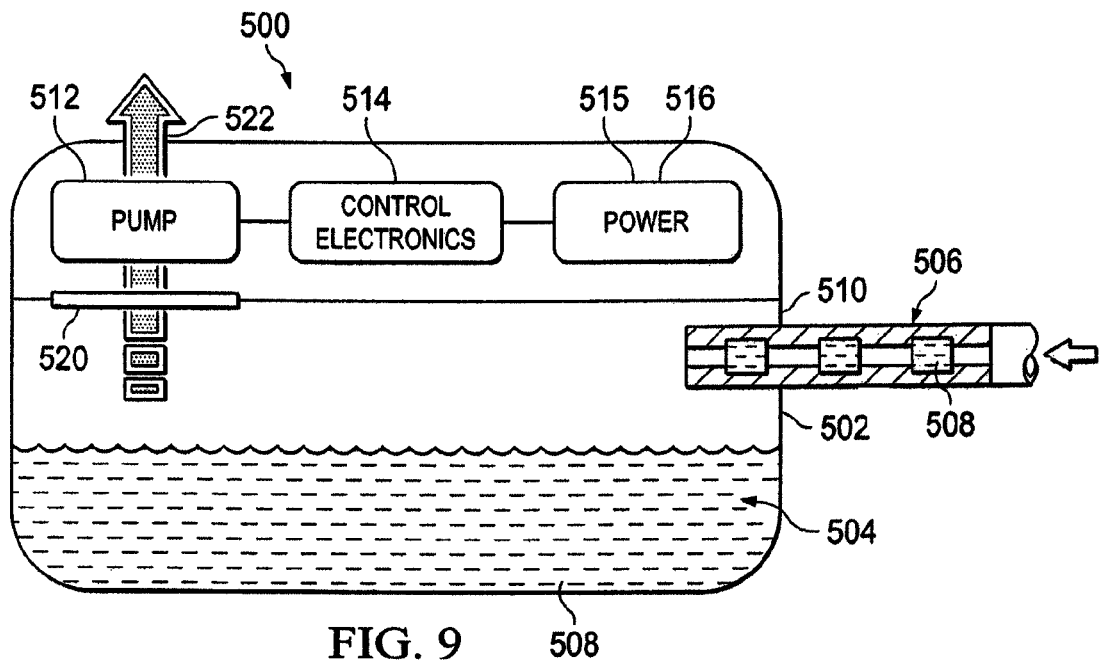
FIG. 9 is a schematic diagram of an illustrative, non-limiting embodiment of a fluid collection system for use as an aspect of a reduced-pressure treatment system.

Referring now primarily to FIGS. 9-12 and initially to FIG. 9, a fluid collection system or subsystem 500 for use with a patient undergoing reduced pressure treatment is presented. The fluid collection system 500 includes a canister body 502 formed with a fluid reservoir 504. A reduced-pressure delivery conduit 506, or conduit, delivers a fluid 508 from a patient to the canister body 502. The reduced-pressure delivery conduit 506 is in fluid communication with the fluid reservoir 504 of the canister body 502. An aperture 510 may be formed in the canister body 502 to allow the fluid 508 to be communicated to the fluid reservoir 504. One or more modules, e.g., a pump 512, pump control electronics 514, and power unit 516, are associated with the canister body 502.

Figure 10:
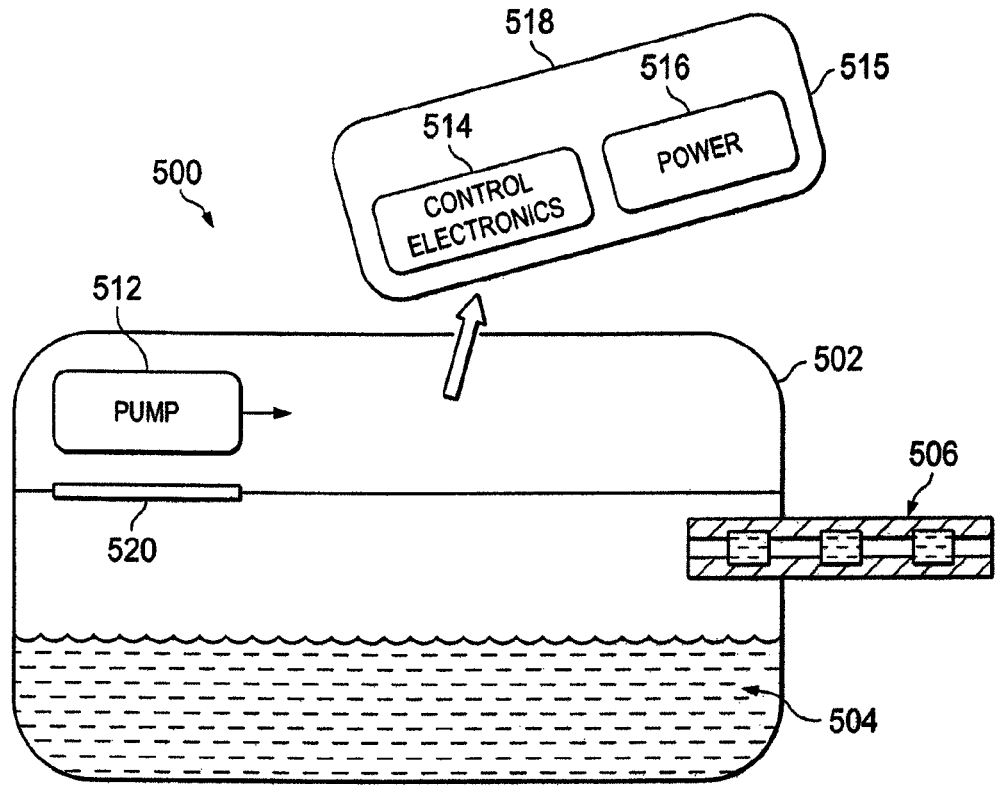
FIG. 10 is a schematic diagram of the fluid collection system of FIG. 9.
Figure 12:
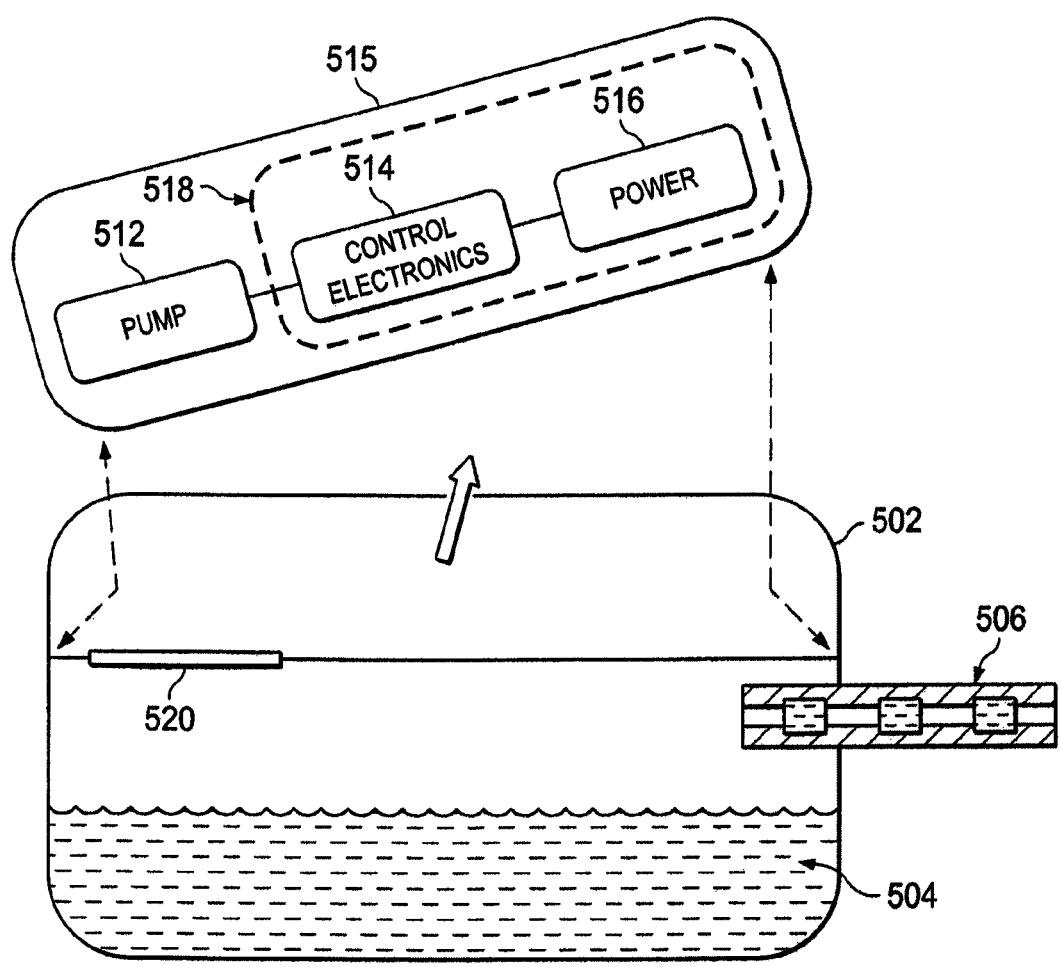
FIG. 12 is a schematic diagram of the fluid collection system of FIG. 9.

The pump 512, pump control electronics 514, and power unit 516 may be disposed within a separate compartment of the canister body 502 or in some illustrative embodiments may be in a separate unit connected to the canister body 502. The pump 512, pump control electronics 514, and power unit 516 may be individual modules 515 or may be coupled in various permutations to form larger modules 515 or units. For example, as shown in FIG. 10, the pump control electronics 514 and power unit 516 may be coupled as a module 515 that is a power-and-control unit 518. As another example, FIG. 12 shows a module 515 formed with the pump 512 and the power-and-control unit 518.

A hydrophobic filter 520 may help safeguard the pump 512 with respect to fluid entry. The pump 512 may be any device for creating reduced pressure. The pump control electronics 514 may be any device or devices for controlling the pump 512. The pump control electronics 514 may be, without limitation, a printed wire assembly (PWA) or an application specific integrated circuit (ASIC) or other control unit.

In operation of the fluid collection system 500, the control electronics 514 may be activated by a user interface (not shown) such that power from the power unit 516 is used to activate the pump 512. The activated pump 512 creates a reduced pressure that is delivered through the filter 520 into the fluid reservoir 504. Exhaust may exit the pump 512 through an exhaust outlet 522 as shown in FIG. 9. The reduced pressure within the fluid reservoir 504 is communicated to the reduced-pressure delivery conduit 506, which is coupled to a fluid receptor (not shown) at the patient. The reduced pressure causes a fluid 508 to be received into the fluid receptor and to flow through the reduced-pressure delivery conduit 506 to the fluid reservoir 504. The fluid receptor may be any device or subsystem for removing fluids from a patient. For example, without limitation, the fluid receptor may be a suction system used in an open body cavity or a manifold, sealing member, and reduced-pressure interface as shown in FIG. 1.

When desired, one or more modules 515, e.g., the pump 512, the pump control electronics 514, or the power unit 516 or a combination thereof, may be removed. For example, FIG. 10 shows the power-and-control unit 518 removed from the canister body 502. After removal, the power-and-control unit 518 may be reconditioned for reuse. Easy removal of the modules 515 facilitates recycling, and recycling of one or more of the modules 515 may be particularly advantageous since they are often the more relatively expensive items of the fluid collection system 500.

Figure 11:
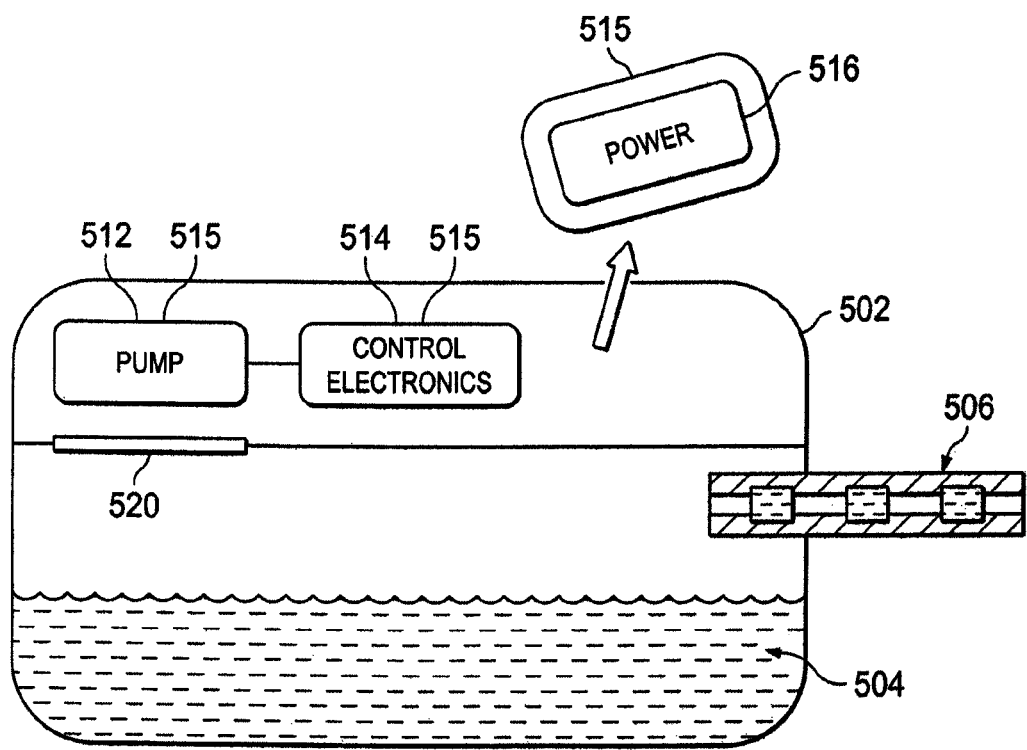
FIG. 11 is a schematic diagram of the fluid collection system of FIG. 9.

After removing the power-and-control unit 518 or other module 515, the fluid reservoir 504 and other remaining aspects of the canister body 502 may be discarded. In FIG. 11, only the power unit 516 is removed. In FIG. 12, a module 515 that includes the pump 512 and the power-and-control unit 518 has been removed. Whatever components or modules 515 are removed, the modules 515 or components are preferably reconditioned and reused with a new canister body (not shown) and any other necessary components. The modules 515 may be releaseably secured to the canister body 502 in a manner that facilitates relatively easy removal by the user. For example, a module 515 may use a snap fit or have only one or two fasteners holding the module 515 to the canister body 502. As additional non-limiting examples, the modules 515 may be retained by a low tack adhesive or an adhesive tape that secures one or more modules 515 to the canister body 502.

Once removed, the modules 515 may be reconditioned for reuse. For example, the modules 515 may be shipped to a recycling center where the modules 515 are reconditioned. It is typically preferable to ship the modules 515 without any substantial biological waste on or in the modules 515. Because the fluid reservoir 504 of the canister body 502 contains biological waste after use, the canister body 502 should not be shipped by routine shipping to a recycling center. The canister body 502 should be handled as a biohazard or treated initially on site. Moreover, at least one safeguard against inadvertently shipping the canister body 502 is desirable.

Figure 13:
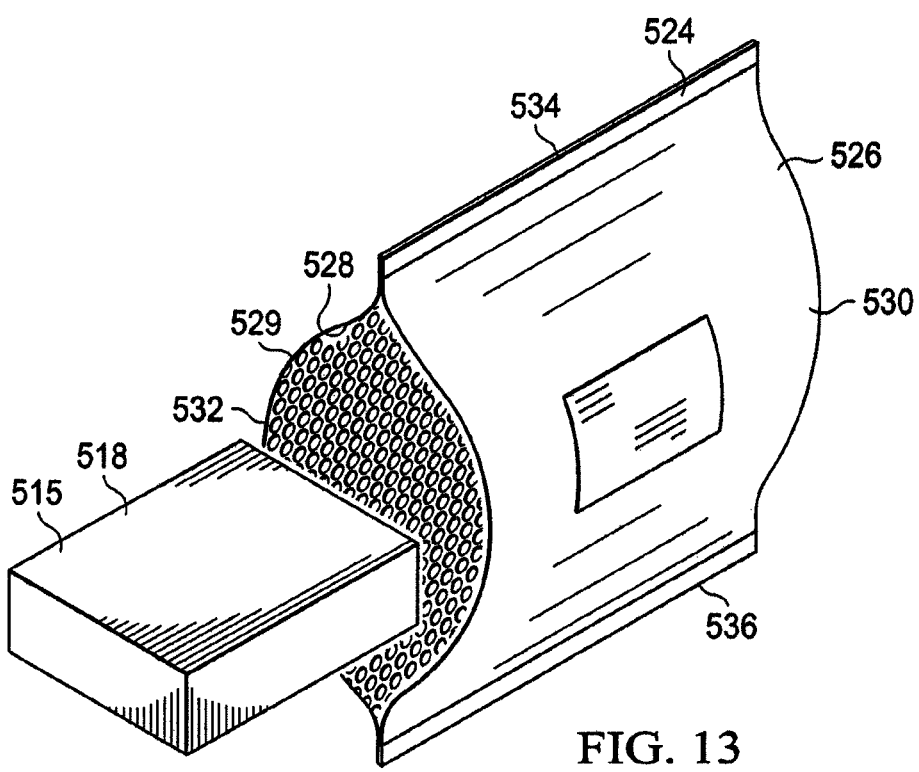
FIG. 13 is a schematic, perspective view of an illustrative, non-limiting embodiment of a fitted shipping receptacle with a unit being inserted.
Figures 14A, 14B:
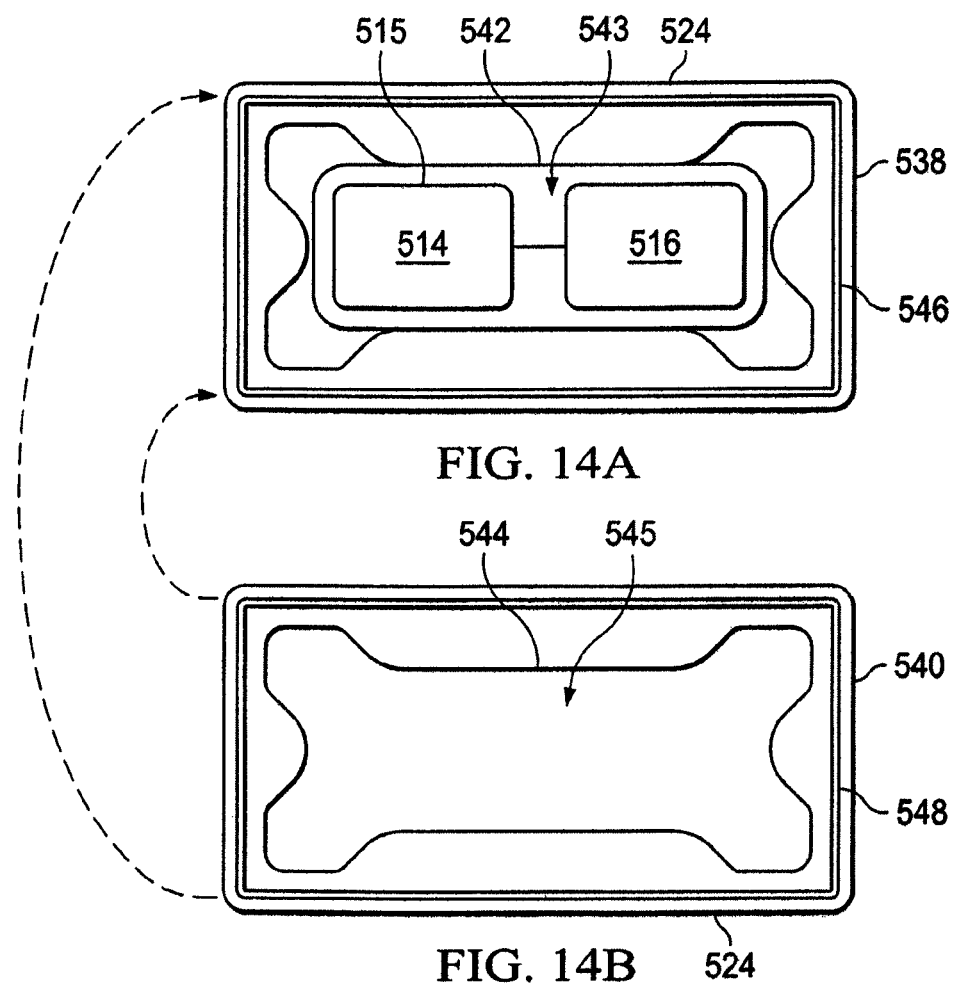
Figure 15:
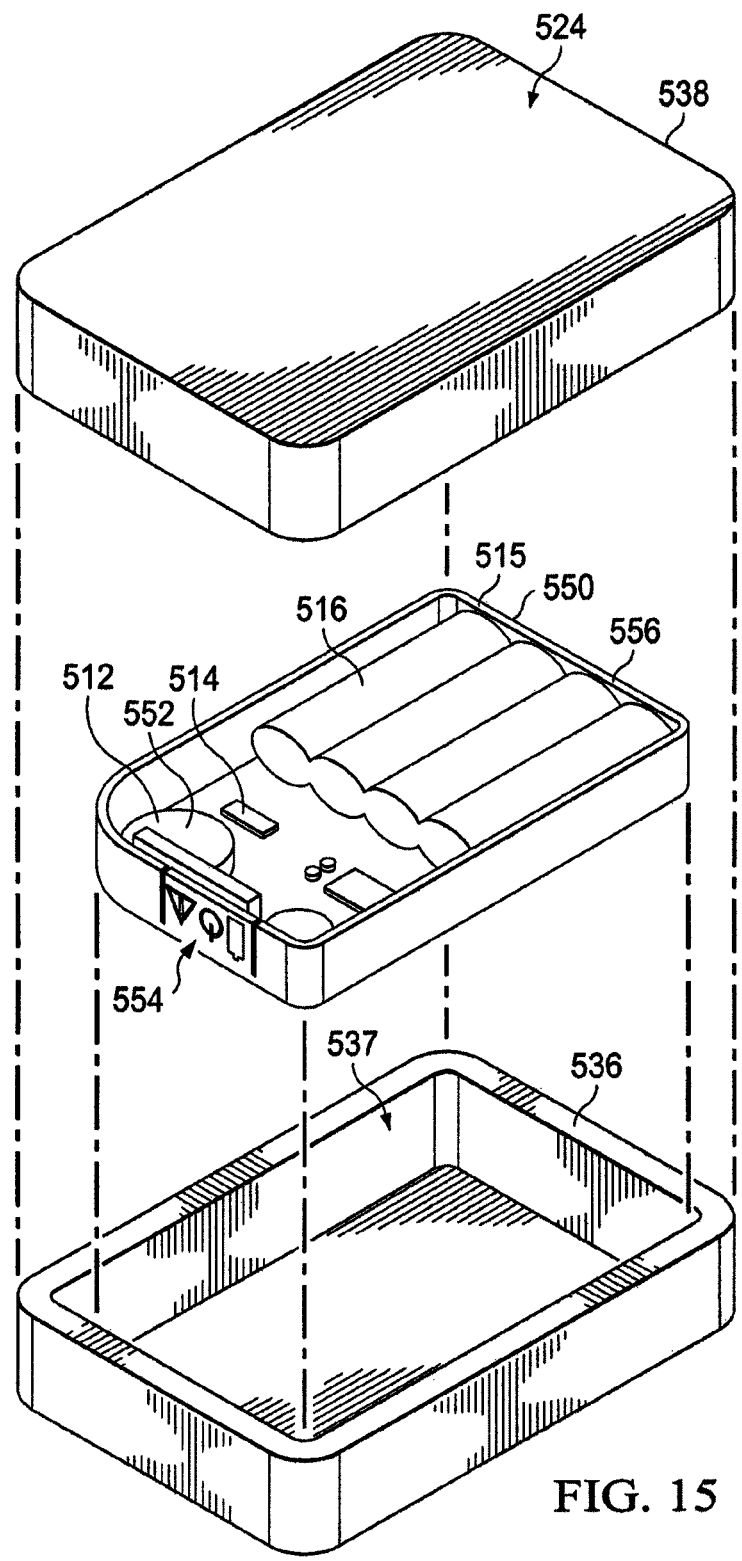
FIG. 15 is a schematic, exploded perspective of an illustrative, non-limiting embodiment of a fitted shipping receptacle shown fitted to receive a components or a unit of a fluid collection system.

Referring now primarily to FIGS. 13-15, as a safeguard to prevent a user from inadvertently shipping the fluid reservoir 504, a fitted shipping receptacle 524 is used that is sized and configured to allow only the desired components or modules 515 to enter the fitted receptacle 524. Put differently, the fitted shipping receptacle 524 disallows the fluid reservoir 504 and the associated portions of the canister body 502 from entering the fitted shipping receptacle 524.

For example, referring now primarily to FIG. 13, the fitted shipping receptacle 524 may be a waterproof, cushioned shipping envelope 526 with an opening 528 large enough to receive an acceptable component or module 515, e.g. power-and-control unit 518, but small enough to prevent the canister body 502 from entering. The cushioned shipping envelope 526 includes cushioning members 529. The cushioned shipping envelope 526 has a first panel 530 and a second panel 532 that are sealed on a first seam 534 and a second seam 536. After inserting the module(s) 515 into the opening 528, the opening 528 is sealed and the module(s) therein may be shipped to the recycling center.

Referring now primarily to FIGS. 14A and 14B, another illustrative, non-limiting embodiment of a fitted shipping receptacle 524 is presented. The fitted shipping receptacle 524 is shown in an unassembled positioned with two members: a first member 538 shown in FIG. 14A and a second member 540 shown in FIG. 14B. The two members 538, 540 are joined as suggested to form the fitted shipping receptacle 524. The fitted shipping receptacle 524 is sized and configured to allow only the desired components or modules 515 of a fluid collection system to be shipped. Without the use of obvious force, the canister body 502 or the fluid reservoir 504 will not fit in the fitted shipping receptacle 524. The members 538 and 540 may be made, for example, from a Styrofoam material or a polymer or any other suitable semi-rigid material.

In one illustrative, non-limiting embodiment, the first member 538 has a first fitted projecting portion 542 that has a first cavity 543. The first cavity 543 is sized and configured to receive at least a portion of the desired components or modules 515, e.g., the pump control electronics 514 and power unit 516. The first fitted projecting portion 542 may deform to receive the module(s) 515 in the first cavity 543. At least a portion of the module(s) 515 may be secured in the first cavity 543 by an interference fit.

Likewise, the second member 540 has a second fitted projecting portion 544 with a second cavity 545 that is also sized and configured to receive at least a portion of the module(s) 515. The second fitted projecting portion 542 may deform to receive the module(s) 515 in the second cavity 545. At least a portion of the module(s) 515 may be secured in the second cavity 545 by an interference fit.

A perimeter 546 of the first member 538 is sized and configured to mate with a perimeter 548 of the second member 540 to form thereby the assembled, fitted shipping receptacle 524. The fitted shipping receptacle 524 is sized and configured to receive the designated components or modules 515 to be shipped. The fitted shipping receptacle 524 is also sized and configured not to close properly with the canister body 502 disposed between the first member 538 and second member 540. The members 538, 540 may be combined and sealed at the perimeters 546, 548 to form the assembled, fitted shipping receptacle 524. For example, the perimeters 546, 548 may be taped, glued, bonded, or otherwise attached. Once loaded with the components or modules 515, the assembled, fitted shipping receptacle 524 may be shipped to a recycling center for reconditioning.

Referring now primarily to FIG. 15, another illustrative, non-limiting embodiment of a fitted shipping receptacle 524 is presented for use with a module 515 or unit 550. The fitted shipping receptacle 524 includes a first member 538 having a first cavity (not explicitly shown) and a second member 540 with a second cavity 537. In this illustrative embodiment, the unit 550 includes a pump 512 or aspects of a pump, such as a first electromagnet 552, control device or pump control electronics 514, and power unit 516. The unit 550 may also include a user interface 554. The unit 550 has a unit housing 556. The first member 538 and second member 540 are sized and configured to receive the unit housing 556 and form an interference fit to secure the unit 550 for shipping. It should be noted that if a canister or fluid reservoir was attached to the unit 550, the unit 550 would not fit into the fitted shipping receptacle 524.

Figure 3:
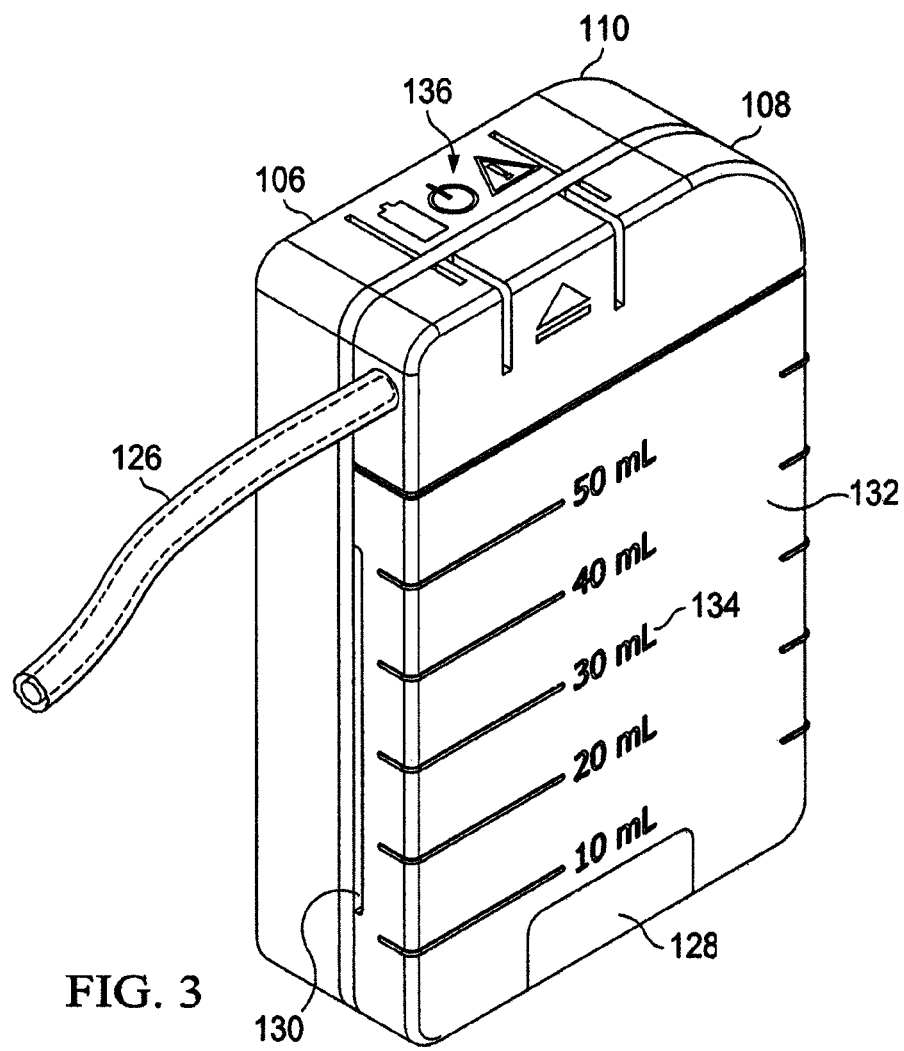
FIG. 3 is a schematic, perspective view of the reduced-pressure treatment device of FIG. 2 shown in an assembled state.

After the unit 550 is used with a canister unit, e.g., the canister unit 108 in FIGS. 2 and 3, the unit 550 is removed, and the unit 550 is placed in between the first member 538 and second member 540. The members 538, 540 are mated to form the fitted shipping receptacle 524. With the unit 550 secured within the fitted shipping receptacle 524, the two members 538 and 540 may be sealed or coupled. The two members 538, 540 may be taped, glued, bonded, or otherwise attached. The fitted shipping receptacle 524 may then be sent to a recycling center for reconditioning of the module 515. After reconditioning, the unit 550 may be used with another canister unit.

Figure 16:
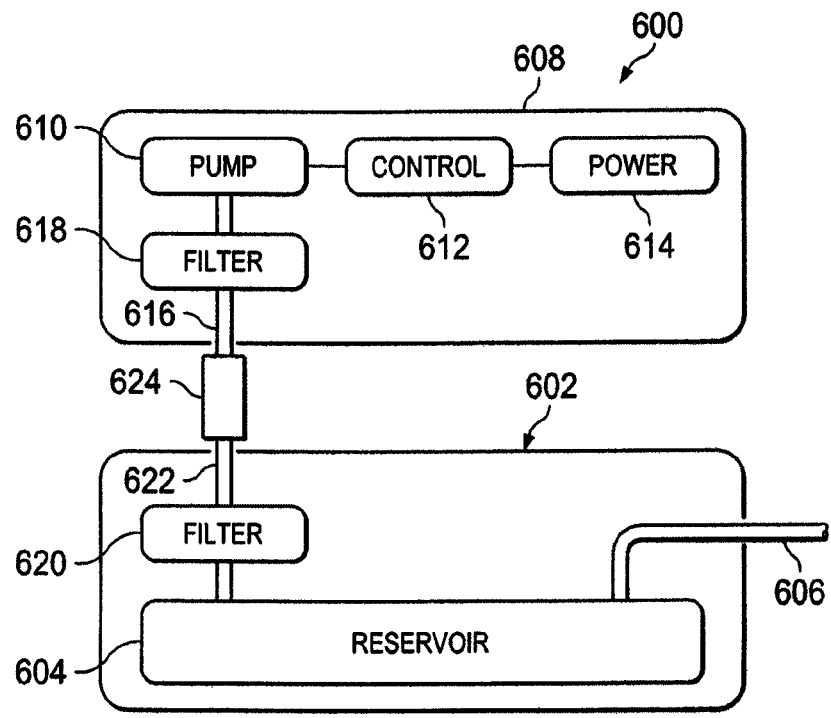
FIG. 16 is a schematic diagram of an illustrative, non-limiting embodiment of a fluid collection system for use with patients undergoing reduced pressure treatment.

Referring now primarily to FIG. 16, a fluid collection system 600 for use with a patient undergoing reduced pressure treatment is presented. The fluid collection system 600 includes a canister unit 602 that includes a fluid reservoir 604. A reduced-pressure delivery conduit 606 delivers fluids from the patient (not shown) to the fluid reservoir 604. The fluids removed and then delivered through reduced-pressure delivery conduit 606 may be from a wound or from a body cavity, such as abdomen, or other location.

The canister unit 602 may be formed by combining two thermoplastic parts. The two thermoplastic parts may be joined and welded together to form the canister unit 602. The canister unit 602 may also be formed by blow molding. Injection molded foam may be blown into a mold to form the canister unit 602. The portion of the foam that first contacts the mold may form an exterior skin with closed cells. The foam that fills the interior portion may have open cells that form a fluid reservoir or volume that is capable of receiving fluids. An integrated filter 620 may be included in the canister unit 602. The integrated filter 620 may be made from sintered polymer. The integrated filter 620 may communicate fluid at any orientation.

The fluid collection system 600 also includes a pump control unit 608 that typically includes a pump 610, a pump control 612 (or pump control electronics 612), and a power unit 614. The pump 610 may be any pump adequate for producing reduced pressure that is delivered to a conduit 616. For example, the pump 610 may be a micro pump, such as a piezoelectric pump, other non-motor pump, or a motor-driven pump. If a micro pump is used, a rapid evacuation port may be added to the canister unit 602 to allow an integrated hospital suction source to be used temporarily to quickly evacuate the fluid reservoir 604 and aspects of the wound dressing. If a piezoelectric pump is used, the piezoelectric pump may be used at different frequencies as a buzzer or vibrating alert system for the fluid collection system 600. A hydrophobic filter 618 may be provided on the conduit 616 to protect the pump 610 from any liquids that might be introduced into the conduit 616. Similarly, a hydrophobic filter 620 may be included on a conduit 622. The conduits 616 and 622 are fluidly coupled and may also be physically coupled by a connection member 624.

The connection member 624 may fluidly and physically couple the pump control unit 608 and the canister unit 602. The connection member 624 is operable to selectively secure the pump control unit 608 and canister unit 602 in relative positions. The connection member 624 is also operable to allow separation of the pump control unit 608 and the canister unit 602 when desired. For example, in one illustrative, non-limiting embodiment, the connection member 624 may be a peg member, e.g., a push-on-and-twist-off type. With such a connection member 624, the pump control unit 608 may be attached or coupled to the canister unit 602 by moving the connection member 624 together with the conduits 616 and 622 so that a coupling is formed. For example, the coupling may be formed by an outwardly biased indention hitting a groove to accomplish a secure lock. Seals on the connection member 624 may provide a fluid seal between the conduits 616, 622 and the connection member 624. The connection member 624 may be formed with a tapered shape that mates with a conduit and forms a seal. The connection member 624 may also be coupled by using a sealing component, e.g., an O ring or other flexible element between the connection member 624 and a conduit. The sealing component may be on the pump control unit 608 or on the connection member 624 before coupling.

When desired, the pump control unit 608 may be separated or uncoupled from the canister unit 602 by pressing a portion of the connection member 624 or twisting and breaking the connection member 624. In one illustrative, non-limiting embodiment, separating the connection member 624 causes both ends of the conduits 616 and 622 to automatically seal. The separated pump control unit 608 may be placed in a fitted shipping receptacle, e.g., the fitted shipping receptacle 524 of FIG. 13, and shipped to a recycling center for reconditioning. After reconditioning, the pump control unit 608 may be used with a new canister unit 602.

Figure 17:
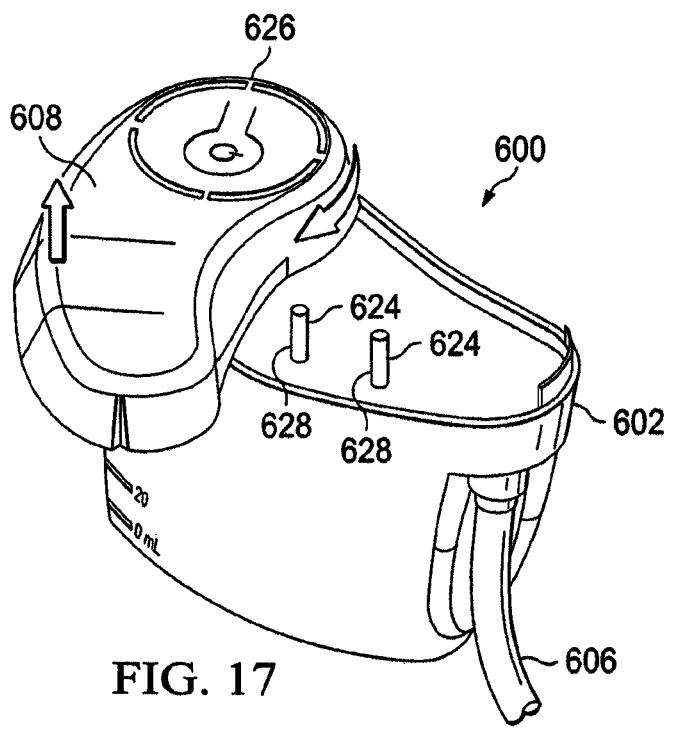
FIG. 17 is a schematic, perspective view of an illustrative, non-limiting embodiment of a fluid collection system for use with patients undergoing reduced pressure treatment.

Referring now primarily to FIG. 17, another illustrative, non-limiting embodiment of a fluid collection system 600 is presented. The fluid collection system 600 includes a canister unit 602 and a pump control unit 608. The fluid collection system 600 of FIG. 17 is analogous to the fluid control system 600 of FIG. 16 in most respects. Thus, a reduced-pressure delivery conduit 606 delivers fluids from a patient to the canister unit 602 and into a fluid reservoir (not shown, but analogous to fluid reservoir 604 in FIG. 16). The pump control unit 608 may be at least partially secured to the canister unit 602 in this embodiment by a swivel connection 626. In this illustrative, non-limiting embodiment, the connection member 624 may be two snap tabs 628. The conduit (analogous to conduits 616 and 622) between the pump control unit 608 and the canister unit 602 may be located within the snap tabs 628 or may be separate from the snap tabs 628.

In operation, according to one illustrative, non-limiting embodiment, the fluid collection system 600 is provided with the pump control unit 608 and canister unit 602 pre-assembled and ready for use. After use, the pump control unit 608 may be twisted about the swivel connection 626, causing the snap tabs 628 to either break or release. A simple tool or other item, such as a coin, may be used to provide leverage to snap the snap tabs 628. When the snap tabs 628 break, an inoperable portion of the snap tab 628 may be left in the canister unit 602. The remaining portion of the snap tab 628 may prevent the canister unit 602 from being reused inadvertently. After breaking the snap tabs 628, the pump control unit 608 may be lifted vertically off of the swivel connection 626. The pump control unit 608 may be swiveled approximately 45 degrees with respect to the canister unit 602 before lifting. Once removed, the pump control unit 608 may be placed in a fitted shipping receptacle and sent to a recycling center for reconditioning and subsequent re-use with a fresh canister unit 602.

The fluid reservoirs, e.g., fluid reservoir 164, 504, 604, herein may be filled with various stabilizing options to reduce the possibility of spillage in the event of a canister failure. For example, without limitation, the following may be used: wicking materials that do not alter the phase of liquids and yet that minimize their mobility; isolyzer sachets and isolyzer scatter coated materials; and oliophillic compounds and coagulants coated onto inert, wicking or isolyzing substrates or the internal surfaces of the canister. These stabilizing options may be accomplished using multi-part molding systems with plasma treatments or other techniques.

Reduced-pressure canisters and methods for recycling are disclosed herein. In one instance, a method for performing multiple reduced pressure treatments on one or more patients includes providing a reduced-pressure treatment system that includes a first canister body, a fluid reservoir, and one or more modules, such as a pump control module. The method involves using the reduced-pressure system and then removing one or more modules and placing the one or more modules in fitted shipping receptacle that disallows shipping of the fluid reservoir. The one or more modules may be reconditioned and coupled to a second canister body. Other systems and methods are disclosed.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, the canister unit 602 of FIGS. 16 and 17 may be formed with a windowed segment to the fluid reservoir 604 that may be covered with the membrane 170 of FIG. 2, i.e., an ultra high moisture-vapor transmission ratio (MVTR) membrane that allows water vapor to pass.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method for performing multiple reduced pressure treatments on one or more patients, the method comprising:
   providing a reduced-pressure treatment system comprising:
      a first canister body formed with a fluid reservoir,
      a conduit fluidly coupled to the fluid reservoir for delivering fluids to the fluid reservoir from a patient,
      a pump attached to the first canister body and operable to develop a reduced pressure within the fluid reservoir,
      a power-and-control unit coupled to the pump for activating and controlling the pump, wherein the power-and-control unit is operable to be removed, and
      a fitted shipping receptacle sized and configured to receive the power-and-control unit, wherein the fitted shipping receptacle is sized and configured to prevent the first canister body from being inserted into the fitted shipping receptacle;
   using the reduced-pressure treatment system to remove fluids from the patient;
   removing the power-and-control unit from the first canister body after use;
   placing the power-and-control unit in the fitted shipping receptacle; and
   shipping the power-and-control unit to a reconditioning center.

2. The method of claim 1, further comprising:
   reconditioning the power-and-control unit; and
   removeably coupling the power-and-control unit to a second canister body.

3. The method of claim 1, further comprising:
   removing the pump from the first canister body after use; and
   placing the pump in the fitted shipping receptacle and shipping to a reconditioning center.

4. The method of claim 3, further comprising:
   reconditioning the pump; and
   removeably coupling the pump to a second canister body.

* * * * *